(12) United States Patent
Shiozaki et al.

(10) Patent No.: US 9,464,105 B2
(45) Date of Patent: Oct. 11, 2016

(54) HYDROXYLATED KRN7000 ANALOGUE AND USE THEREOF

(71) Applicant: RIKEN, Wako-shi, Saitama (JP)

(72) Inventors: Masao Shiozaki, Wako (JP); Takuya Tashiro, Wako (JP); Kenji Mori, Wako (JP); Tomokuni Shigeura, Wako (JP); Hiroshi Watarai, Wako (JP); Masaru Taniguchi, Wako (JP)

(73) Assignee: RIKEN, Wako (JP)

( * ) Notice: Subject to any disclaimer, the term of this patent is extended or adjusted under 35 U.S.C. 154(b) by 0 days.

(21) Appl. No.: 14/419,198

(22) PCT Filed: Aug. 2, 2013

(86) PCT No.: PCT/JP2013/071063
§ 371 (c)(1),
(2) Date: Feb. 2, 2015

(87) PCT Pub. No.: WO2014/021464
PCT Pub. Date: Feb. 6, 2014

(65) Prior Publication Data
US 2015/0218199 A1    Aug. 6, 2015

(30) Foreign Application Priority Data
Aug. 3, 2012    (JP) ................ 2012-173278

(51) Int. Cl.
| | | |
|---|---|---|
| *C07H 15/06* | (2006.01) | |
| *C07H 15/04* | (2006.01) | |
| *C12N 5/06* | (2006.01) | |
| *C12N 5/0784* | (2010.01) | |
| *A61K 35/17* | (2015.01) | |
| *A61K 35/15* | (2015.01) | |
| *A61K 35/12* | (2015.01) | |

(52) U.S. Cl.
CPC .............. *C07H 15/06* (2013.01); *A61K 35/15* (2013.01); *A61K 35/17* (2013.01); *C07H 15/04* (2013.01); *C12N 5/064* (2013.01); *A61K 2035/122* (2013.01); *C12N 2501/999* (2013.01)

(58) Field of Classification Search
None
See application file for complete search history.

(56) References Cited

U.S. PATENT DOCUMENTS

| | | |
|---|---|---|
| 5,849,716 A | 12/1998 | Akimoto et al. |
| 5,936,076 A | 8/1999 | Higa et al. |
| 8,883,746 B2 | 11/2014 | Kang et al. |
| 2010/0104590 A1 | 4/2010 | Kang et al. |

FOREIGN PATENT DOCUMENTS

| | | |
|---|---|---|
| EP | 0609437 A1 | 8/1994 |
| EP | 0666268 A1 | 8/1995 |
| JP | H05-009193 A | 1/1993 |
| JP | H05-059081 A | 3/1993 |
| WO | 94/09020 A1 | 4/1994 |
| WO | 2008/082156 A1 | 7/2008 |

OTHER PUBLICATIONS

Shiozaki et al., Carbohydrate Research, 2013, vol. 370, pp. 46-66.*
Zhan et al., Journal of Natural Products, 2003, vol. 66, pp. 1013-1016.*
Aspeslagh et al., *The EMBO Journal*, 30: 2294-2305 (2011).
Borg et al., *Nature*, 448: 44-49 (2007).
Jervis et al., *J. Org. Chem.*, 76: 320-323 (2011).
Kawano et al., *Science*, 278: 1626-1629 (1997).
Li et al., *Immunology*, 127: 216-225 (2008).
Li et al., *PNAS*, 107(29): 13010-13015 (2010).
Liang et al., *J. Am. Chem. Soc.*, 130: 12348-12354 (2008).
Liu et al., *Bioorg. Med. Chem. Lett.*, 18(10): 3052-3055 (2008).
Mallevaey et al., *Immunity*, 31(1): 60-71 (2009).
Scott-Browne et al., *Nature Immunology*, 8(10): 1105-1113 (2007).
Trappeniers et al., *J. Am. Chem. Soc.*, 130: 16468-16469 (2008).
Yu et al., *The Journal of Immunology*, 187: 2079-2083 (2011).
Zhou et al., *Organic Letters*, 4(8): 1267-1270 (2002).
La Clair et al., *Bioorganic & Medicinal Chemistry*, 19(22): 6645-6653 (2011).
Shiozaki et al., *Carbohydrate Research*, 370: 46-66 (2013).
Zhan et al., *Journal of Natural Products*, 66(7): 1013-1016 (2003).
European Patent Office, Supplementary European Search Report in European Patent Application No. 13825619 (Jan. 19, 2016).

\* cited by examiner

*Primary Examiner* — Traviss C McIntosh, III
(74) *Attorney, Agent, or Firm* — Leydig, Voit & Mayer, Ltd.

(57) ABSTRACT

The invention provides a compound represented by the formula (I)

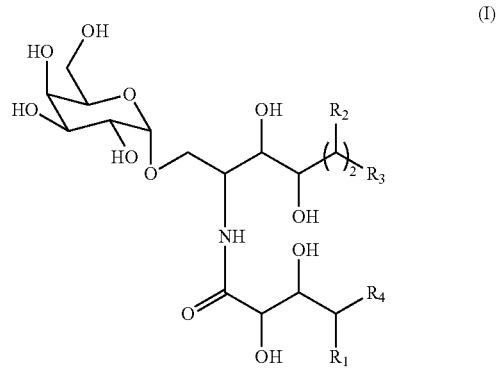

wherein $R_1$ is a hydrogen atom or a hydroxyl group; two $R_2$ are the same or different and each is a hydrogen atom or a hydroxyl group; $R_3$ is a hydrocarbon group having 8-14 carbon atoms, which optionally has substituent(s); and $R_4$ is a hydrocarbon group having 18-24 carbon atoms, which optionally has substituent(s), or a salt thereof. The invention also provides a method of treating an autoimmune disease or suppressing immunity by administering the aforementioned compound or a salt thereof to a patient in need thereof.

14 Claims, 4 Drawing Sheets

HYDROXYLATED KRN7000 ANALOGUE AND USE THEREOF

CROSS-REFERENCE TO RELATED APPLICATIONS

This patent application is the U.S. national phase of International Patent Application No. PCT/JP2013/071063, filed Aug. 2, 2013, which claims the benefit of Japanese Patent Application No. 2012-173278, filed on Aug. 3, 2012, which are incorporated by reference in their entireties herein.

TECHNICAL FIELD

The present invention relates to a novel hydroxylated KRN7000 analog and use thereof. More particularly, the present invention relates to a hydroxylated KRN7000 analog wherein a hydroxyl group is introduced into a phytosphingosine and/or amide side chain, a production method thereof, and a pharmaceutical use thereof.

BACKGROUND ART

α-Galactosylceramides, typified by agelasphins, are glycolipids isolated from extracts from *Agelas mauritianus*, a kind of marine sponge, and have been reported to potently activate NKT cells (non-patent document 1).

KRN7000 is taken by antigen presenting cells (APC) represented by dendritic cell (DC) and the like, and presented on a cellular membrane by CD1d protein similar to major histocompatibility complex (MHC) class I molecule. NKT cells are activated by recognizing a complex of the thus-presented CD1d protein and α-galactosylceramide by using TCR, whereby cytokines of immunity control system are produced. As the cytokine, Th1 type cytokine (mainly interferon (IFN)-γ) that promotes immunoactivating action and Th2 type cytokine (mainly interleukin (IL)-4) that promotes immunosuppressive action are known (non-patent document 2). Many researchers consider that biased secretion of Th1 type and Th2 type cytokines from NKT cells, namely, whether the secretion is biased to the Th1 type or Th2 type determines whether use as a cancer-inhibiting drug or immunosuppressant can be expected, and the index is currently being acknowledged widely as an initial index of use development in the world.

Heretofore, various α-galactosylceramide analogs have been synthesized, and the correlation between the structure and the activity has been researched. A compound known as KRN7000 which is one of α-galactosylceramides (non-patent document 3) is a compound developed by Kirin Brewery Co. through synthesis and studies of agelasphins, and shows a highly strong anti-tumor activity.

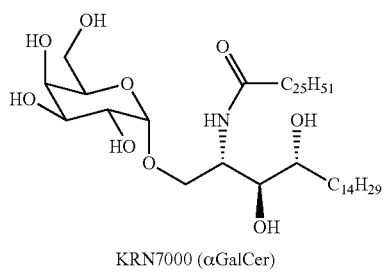

KRN7000 (αGalCer)

On the other hand, OCH which is a truncated analog of KRN7000 (non-patent documents 4-8) and RCAI-80 which is an esterified analog of KRN7000 (non-patent document 9) are biased to the Th2 type, and their effect as an immunosuppressant is expected.

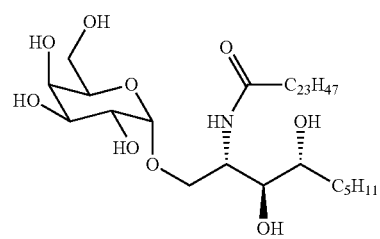

OCH

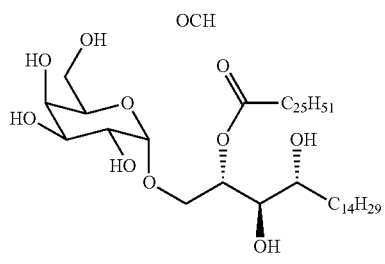

RCAI-80

At present, as an immunosuppressant, adrenocortical hormone, metabolic antagonist, alkylating agent, alkaloid, antibiotic, antilymphocyte globulin, anti-CD3 monoclonal antibody and the like are known, and they are used as therapeutic drugs for autoimmune diseases, allergic diseases, organ transplantation and the like.

For example, cyclosporine A (CsA) is a superior medicament currently used for preventing rejection of transplanted organs. FK506 (tacrolimus hydrate) is used for preventing rejection of transplanted liver. CsA and FK506 act by preventing many natural protective substances in the immune system of the body from rejecting the transplanted foreign protein. CsA is also used for the treatment of severe psoriasis and the treatment of atopic dermatitis. While CsA and FK506 are effective for fighting the transplantation rejection, they are known to cause some undesired side effects including renal toxicity, neurotoxicity and gastrointestinal uncomfortable feeling. While FTY720 is a pharmaceutical product expected to provide a new treatment method of multiple sclerosis, its effectiveness for other autoimmune diseases is limited. That is, conventional immunosuppressants are not necessarily satisfactory in terms of effectiveness, sustainability, side effects and the like, and a more superior immunosuppressant, preferably an immunosuppressant having an action mechanism different from those of conventional immunosuppressants, is demanded.

DOCUMENT LIST

Non-Patent Documents non-patent document 1: Science, 1997, 278, 1626-1629
non-patent document 2: Science, 1997, 277, 339-345
non-patent document 3: J. Med. Chem. 1995, 38, 2176-2187
non-patent document 4: Nature, 2001, 413, 531-534
non-patent document 5: Curr. Top. Med. Chem. 2004, 4, 561-567
non-patent document 6: J. Clin. Invest. 2004, 113, 1631-1640 non-patent document 7: J. Org. Chem. 2005, 70, 10260-10270 non-patent document 8: J. Org. Chem. 2005, 70, 2398-2401 non-patent document 9: Carbohydr. Res. 2010, 1663-1684

SUMMARY OF THE INVENTION

Problems to be Solved by the Invention

The present invention has been made in view of such actual condition, and its problem to be solved is provision of a novel Th2 type-biased α-galactosylceramide analog expected to show an immunosuppressive effect. Also, the present invention aims to provide a medicament containing such an α-galactosylceramide analog.

Means of Solving the Problems

To solve the above-mentioned problem, the present inventors took note of compound OCH which is a truncated analog of KRN7000. The compound OCH is a promising candidate medicament for the treatment of autoimmune diseases, immunosuppression relating to the organ transplantation, treatment of inflammation state and the like. The lipophilicity of compound OCH is considered to have decreased, in which case the hydrophilicity is considered to have increased conversely. That is, KRN7000 analogs having improved hydrophilicity may be useful, like compound OCH, for the treatment of autoimmune diseases, immunosuppression relating to organ transplantation, treatment of inflammation state and the like, which are biased to the Th2 type. KRN7000 contains phytosphingosine, and is known to form a hydrogen bond between amide N—H hydrogen on the phytosphingosine and oxygen at the 156th threonine residue of mouse CD1d (154th threonine residue in human CD1d). By X-ray crystallography, it is known that a definite hydrogen bond is formed between the Arg79 residue of mouse CD1d and 3'-OH of KRN7000 phytosphingosine, and the Asp80 residue forms a hydrogen bond with 3'-OH and 4'-OH of phytosphingosine (Natur Immunol. 2005, 6, 810-818; Natur Immunol. 2005, 6, 819-826; Nature 2007, 448, 44-49; J. Immunity, 2009, 31, 47-59). It was sufficiently predicted from the similarity to the hydrogen bond between KRN7000 and CD1d that a similar hydrogen bond is present between compound OCH and CD1d. The present inventors synthesized various hydroxylated KRN7000 analogs wherein one or plural hydroxyl groups are introduced into phytosphingosine, which is the main chain of KRN7000, and/or amide side chain, and examined whether hydrophilicity can be increased. Furthermore, they have examined whether the obtained analog is Th2-biased, and obtained a compound showing cytokine secretion biased to the Th2 type, particularly a compound showing suppressed production of Th1 type cytokine and cytokine secretion biased to the Th2 type, and confirmed that the compound has an immunosuppressive effect, which resulted in the completion of the present invention.

Accordingly, the present invention provides the following.

[1] A compound represented by the formula (I)

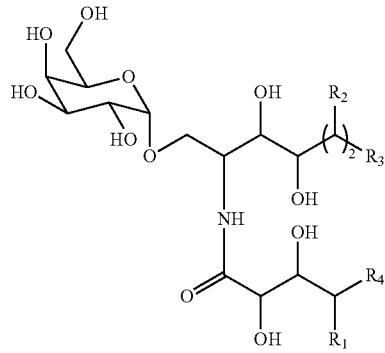

(I)

wherein $R_1$ is a hydrogen atom or a hydroxyl group;

two $R_2$ are the same or different and each is a hydrogen atom or a hydroxyl group;

$R_3$ is a hydrocarbon group having 8-14 carbon atoms, which optionally has substituent(s); and $R_4$ is a hydrocarbon group having 18-24 carbon atoms, which optionally has substituent(s) (hereinafter to be also referred to as compound (I)), or a salt thereof.

[2] The compound of the above-mentioned [1], wherein $R_3$ is a $C_{8-14}$ alkyl group, a $C_{8-14}$ alkenyl group or a $C_{8-14}$ alkynyl group, each of which optionally has substituent(s), or a salt thereof.

[3] The compound of the above-mentioned [1], wherein $R_4$ is a $C_{18-24}$ alkyl group, a $C_{18-24}$ alkenyl group or a $C_{18-24}$ alkynyl group, each of which optionally has substituent(s), or a salt thereof.

[4] The compound of the above-mentioned [1], wherein $R_1$ is a hydrogen atom, two $R_2$ are hydroxyl groups, $R_3$ is a $C_{8-14}$ alkyl group, and $R_4$ is a $C_{18-24}$ alkyl group, or a salt thereof.

[5] The compound of the above-mentioned [1], wherein $R_1$ is a hydrogen atom, two $R_2$ are hydrogen atoms, $R_3$ is a $C_{8-14}$ alkyl group, and $R_4$ is a $C_{18-24}$ alkyl group, or a salt thereof.

[6] The compound of the above-mentioned [1], wherein $R_1$ is a hydroxyl group, two $R_2$ are hydrogen atoms, $R_3$ is a $C_{8-14}$ alkyl group, and $R_4$ is a $C_{18-24}$ alkyl group, or a salt thereof.

[7] The compound of the above-mentioned [1], which is

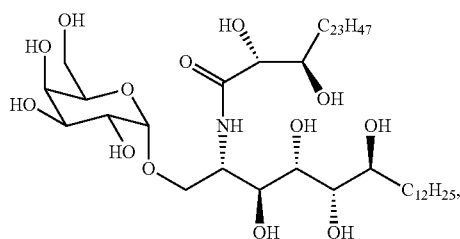

-continued

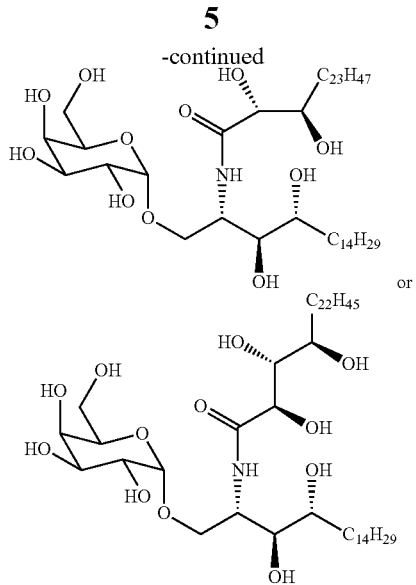

or a salt thereof.

[8] A medicament comprising the compound of any of the above-mentioned [1]-[7] or a salt thereof.
[9] A Th2 type cytokine secretion promoter comprising the compound of any of the above-mentioned [1]-[7] or a salt thereof.
[10] The medicament of the above-mentioned [8], which is a therapeutic drug for an autoimmune disease.
[11] The medicament of the above-mentioned [8], which is an immunosuppressant.
[12] A human dendritic cell pulsed with the compound of any of the above-mentioned [1]-[7] or a salt thereof.
[13] An immunosuppressant comprising the human dendritic cell of the above-mentioned [12].
[14] A therapeutic drug for an autoimmune disease, comprising the human dendritic cell of the above-mentioned [12].
[15] A method of promoting Th2 type cytokine secretion, comprising administering an effective amount of the compound of any of the above-mentioned [1]-[7] or a salt thereof to a patient in need thereof.
[16] A method of treating an autoimmune disease, comprising administering an effective amount of the compound of any of the above-mentioned [1]-[7] or a salt thereof to a patient in need thereof.
[17] A method of suppressing immunity, comprising administering an effective amount of the compound of any of the above-mentioned [1]-[7] or a salt thereof to a patient in need thereof.
[18] A method of suppressing immunity, comprising administering an effective amount of the human dendritic cell of the above-mentioned [12] to a patient in need thereof.
[19] A method of treating an autoimmune disease, comprising administering an effective amount of the human dendritic cell of the above-mentioned [12] to a patient in need thereof.
[20] The compound of any of the above-mentioned [1]-[7] or a salt thereof for promoting Th2 type cytokine secretion.
[21] The compound of any of the above-mentioned [1]-[7] or a salt thereof for suppressing immunity.
[22] The compound of any of the above-mentioned [1]-[7] or a salt thereof for treating an autoimmune disease.

Effect of the Invention

Various hydroxylated KRN7000 analogs wherein one or plural hydroxyl groups have been introduced into the main chain phytosphingosine and/or amide side chain show cytokine secretion biased to the Th2 type. The compound of the present invention having an IFN-γ/IL-4 ratio biased to the IL-4 which is important for an immunosuppressive effect and the like, is useful as a therapeutic drug for autoimmune diseases or an immunosuppressant.

DESCRIPTION OF EMBODIMENTS

Figure 1:
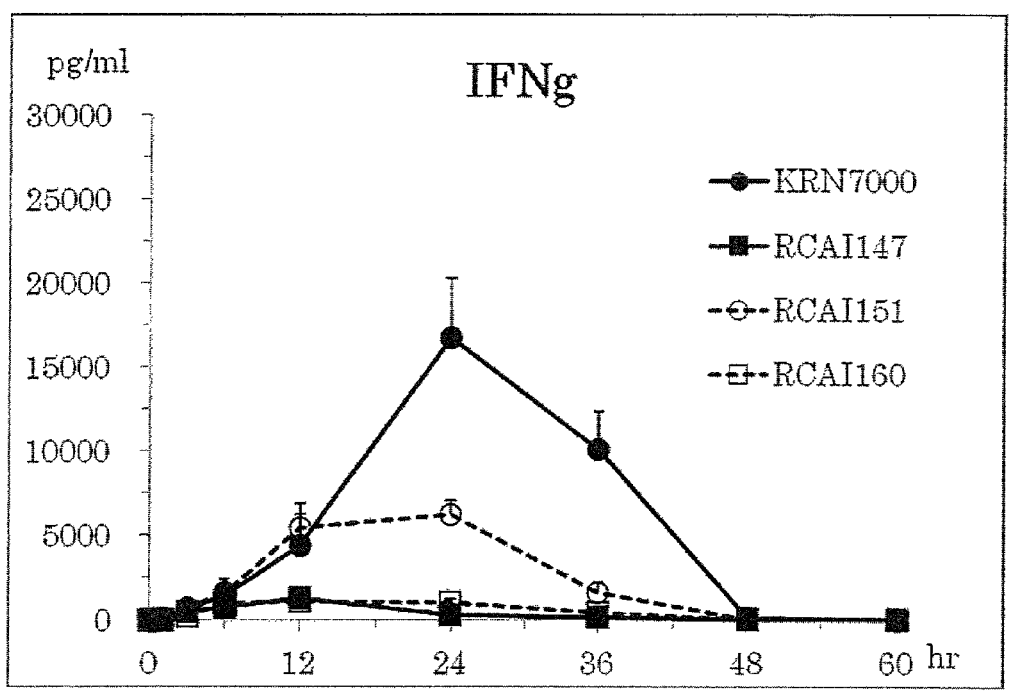
FIG. 1 is a graph showing changes in the IFN-γ (IFNg) concentration of mouse plasma after lapse of an indicated time after intravenous administration of various glycolipids to mouse.

The present invention is explained in detail in the following by referring to preferable embodiments.
First, the definitions of the symbols to be used in each formula of the present specification are explained.
$R_1$ is a hydrogen atom or a hydroxyl group.
Two $R_2$ are the same or different and each is a hydrogen atom or a hydroxyl group.
$R_3$ is a hydrocarbon group having 8-14 carbon atoms. The "hydrocarbon group having 8-14 carbon atoms" is a concept encompassing a $C_{8-14}$ alkyl group, a $C_{8-14}$ alkenyl group, a $C_{8-14}$ alkynyl group, a $C_{8-14}$ cycloalkyl group, a $C_{8-14}$ cycloalkenyl group, and even a $C_{8-14}$ aryl group, which may be linear, branched or cyclic, or may be a saturated hydrocarbon group or an unsaturated hydrocarbon group, and optionally having an unsaturated bond in a molecule or at the terminal. Among these, preferred as $R_3$ are a $C_{8-14}$ alkyl group, a $C_{8-14}$ alkenyl group, and a $C_{8-14}$ alkynyl group, and more preferred is a $C_{11-13}$ alkyl group. As $R_3$, specifically, $—C_{12}H_{25}$ and the like can be mentioned.
$R_4$ is a hydrocarbon group having 18-24 carbon atoms. The "hydrocarbon group having 18-24 carbon atoms" is a concept encompassing a $C_{18-24}$ alkyl group, a $C_{18-24}$ alkenyl group, a $C_{18-24}$ alkynyl group, a $C_{18-24}$ cycloalkyl group, a $C_{18-24}$ cycloalkenyl group, and even a $C_{18-24}$ aryl group, which may be linear, branched or cyclic, or may be a saturated hydrocarbon group or an unsaturated hydrocarbon group, and optionally has an unsaturated bond in a molecule or at the terminal. Among these, preferred as $R_4$ are a $C_{19-23}$ alkyl group, a $C_{19-23}$ alkenyl group, and a $C_{19-23}$ alkynyl group, more preferred is a $C_{21-23}$ alkyl group. Specific examples of $R_4$ include $—C_{22}H_{45}$ and the like.
The hydrocarbon group for $R_3$ or $R_4$ is preferably linear.
The hydrocarbon groups for $R_3$ and $R_4$ may each independently have substituent(s). When the hydrocarbon group for $R_3$ or $R_4$ has substituent(s), examples of the substituent include an electron-donating group such as a halogen atom (preferably chlorine atom, fluorine atom); an alkoxy group (preferably carbon number of 1-24, more preferably carbon number of 1-16, still more preferably carbon number of 1-10, particularly preferably carbon number of 1-4) such as methoxy, ethoxy, propoxy, isopropoxy, butoxy, tert-butoxy and the like; an aryloxy group (preferably carbon number of 6-14) such as phenoxy and the like; a hydroxyl group; an amino group; an alkylamino group such as methylamino, dimethylamino, ethylamino, diethylamino and the like; a cycloalkylamino group; an alkylcarbonylamino group such as acetamide and the like; a cycloalkylcarbonylamino group; arylcarbonylamino group (preferably, an arylcarbonylamino group having a carbon number of 7-15, wherein the aryl moiety is an aryl group having a carbon number of 6-14) such as benzoylamino and the like, and the like, further, an electron-withdrawing group such as a carboxyl group; an alkoxycarbonyl group; an acyl group (acyl group is as mentioned below, preferably an acyl group having a carbon number of 2-25, more preferably an alkyl-carbonyl group wherein the alkyl moiety is a straight chain or branched alkyl group having a carbon number of 1-24); carbamoyl; trifluoromethyl and the like. The position and number of the substituents are not particularly limited, and one to substitutable maximum number of substituents may be present at substitutable position(s). When one or more substituents are present, they may be the same or different.

The hydrocarbon group for $R_3$ or $R_4$ is preferably unsubstituted.

$R_3$ is preferably an unsubstituted $C_{8-14}$ alkyl group, a $C_{8-14}$ alkenyl group or a $C_{8-14}$ alkynyl group, more preferably an unsubstituted $C_{8-14}$ alkyl group.

$R_4$ is preferably an unsubstituted $C_{18-24}$ alkyl group, a $C_{18-24}$ alkenyl group or a $C_{18-24}$ alkynyl group, more preferably an unsubstituted $C_{18-24}$ alkyl group.

The "acyl group" in the present specification is, for example, formyl; an acyl group having a carbon number of 2-25 [an alkyl-carbonyl group (e.g. an alkyl-carbonyl group wherein the alkyl moiety is a straight chain or branched alkyl group having a carbon number of 1-24 (preferably 1-) (e.g., acetyl, propionyl, butyryl, isobutyryl, valeryl, pivaloyl, hexanoyl)); a cycloalkyl-carbonyl group (e.g., a cycloalkyl-carbonyl group wherein the cycloalkyl moiety is a cycloalkyl group having a carbon number of 3-10); an alkenyl-carbonyl group (e.g., an alkenyl-carbonyl group wherein the alkenyl moiety is a straight chain or branched alkenyl group having a carbon number of 2-2 (e.g., acryloyl, methacryloyl)); an aryl-carbonyl group (e.g., an aryl-carbonyl group wherein the aryl moiety is an aryl group having a carbon number of 6-14 (e.g., benzoyl, naphthoyl)) and the like. The aryl group of the aryl-carbonyl group is, for example, a monocyclic-tricyclic aromatic hydrocarbon group, and specific examples include phenyl, naphthyl, anthryl and phenanthryl. Of these, as the acyl group, formyl, acetyl, propionyl, butyryl, isobutyryl, benzoyl, naphthoyl and the like are preferable, and acetyl and benzoyl are more preferable.

Examples of the alkyl moiety of the above-mentioned alkylamino group and alkylcarbonylamino group include a straight chain or branched alkyl group (preferably carbon number of 1-24, more preferably carbon number of 1-16, still more preferably carbon number of 1-10, particularly preferably carbon number of 1-4) such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and the like.

Examples of the cycloalkyl moiety of the above-mentioned cycloalkylamino group and cycloalkylcarbonylamino group include a cycloalkyl group (preferably carbon number of 3-24, more preferably carbon number of 3-16, still more preferably carbon number of 3-10, particularly preferably carbon number of 3-6) such as cyclopentyl, cyclohexyl and the like.

Examples of the alkoxy moiety of the above-mentioned alkoxycarbonyl group include those similar to the above-mentioned alkoxy group.

The above-mentioned substituents may be further substituted at substitutable position(s) by at least one kind from halogen, an alkyl group, a cycloalkyl group, an alkenyl group, an alkynyl group, a phenyl group, an alkoxy group, a hydroxyl group, an amino group, an alkylamino group and a cycloalkylamino group.

Examples of the halogen, alkoxy group, alkylamino group and cycloalkylamino group include those similar to the above.

Examples of the alkyl group include an alkyl group (preferably carbon number of 1-24, more preferably carbon number of 1-16, still more preferably carbon number of 1-10, particularly preferably carbon number of 1-4) such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl and the like.

Examples of the cycloalkyl group include a cycloalkyl group (preferably carbon number of 3-24, more preferably carbon number of 3-16, still more preferably carbon number of 3-10, particularly preferably carbon number 3-6) such as cyclopentyl, cyclohexyl and the like.

Examples of the alkenyl group include an alkenyl group (preferably carbon number of 2-24, more preferably carbon number of 2-16, still more preferably carbon number of 2-10, particularly preferably carbon number of 2-4) such as vinyl, propenyl, butenyl and the like.

Examples of the alkynyl group include an alkynyl group (preferably carbon number of 2-24, more preferably carbon number of 2-16, still more preferably carbon number of 2-10, particularly preferably carbon number of 2-4) such as ethynyl, propargyl, butynyl, pentynyl and the like.

In the present invention, the a configuration is employed from among the stereoisomers derived from the cyclic structure of sugar (galactopyranose).

When compound (I) has a stereoisomer derived from a structure of the agricon part other than a cyclic structure of sugar (e.g., asymmetric carbon etc. of the agricon part other than the cyclic structure of sugar), any isomers are also encompassed in the present invention, which may be a mixture (including racemate) of two or more kinds of isomers at any ratio.

Particularly, compound (I) contains an optical isomer derived from the asymmetric carbon of an agricon part other than the cyclic structure of sugar. In the present invention, compound (I) may be a single optically active form or a mixture of two or more kinds of optically active forms at any ratio (including racemates).

Salts of compound (I) are preferably pharmaceutically acceptable salts; examples include inorganic acid salts such as hydrochlorides, hydrobromides, hydroiodides, sulfates, nitrates, and phosphates; organic acid salts such as succinates, fumarates, acetates, methanesulfonates, and toluenesulfonates; alkali metal salts such as sodium salts and potassium salts; alkaline earth metal salts such as magnesium salts and calcium salts; ammonium salts such as ammonium salts and alkylammonium salts; and the like.

Specific examples of preferable compound (I) of the present invention are as described below, which are not to be construed as limitative.

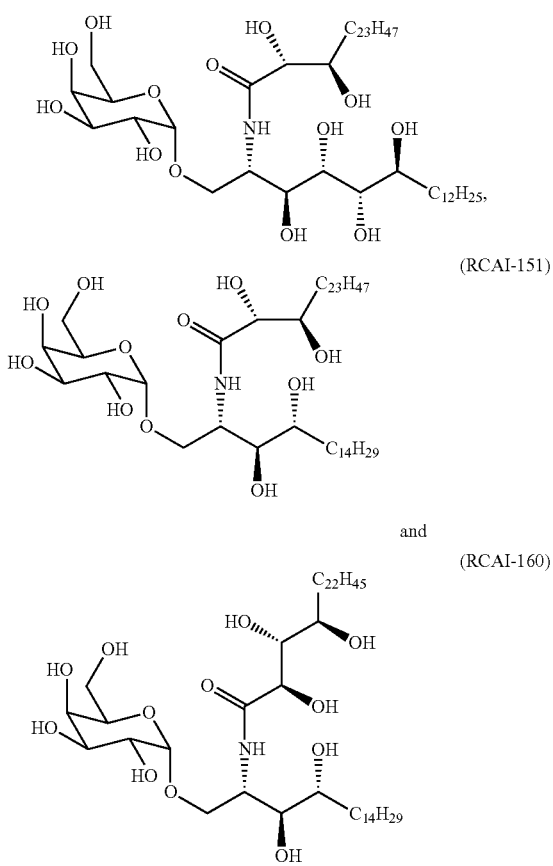

They are more preferably RCAI-147 and RCAI-160.

The production method of compound (I) of the present invention is explained below.

Compound (I) can be produced according to the method described in the following Scheme or a method analogous thereto, but the method is not limited thereto, and can be modified as appropriate on demand. Examples of such modification include alkylation, acylation, amination, imination, halogenation, reduction, oxidation and the like, for which reactions and methods generally used in the field are utilized. In this case, depending on the kind of the functional group, it is sometimes effective for production techniques to substitute the functional group in the stage of starting material or intermediate by a suitable protecting group (group easily convertible to the functional group). Chemical properties of protecting groups, method of introduction thereof, and removal thereof are described in detail in, for example, T. Greene and P. Wuts "Protective Groups in Organic Synthesis" ($3^{rd}$ ed.), John Wiley & Sons NY (1999).

Particularly, a hydroxyl-protecting group is used in the present invention. The protecting group is appropriately selected according to the desired reaction. Examples of the hydroxyl-protecting group include benzyl, 4-methoxybenzyl (i.e., p-methoxybenzyl (PMB)), methoxyethoxymethyl, tetrahydropyranyl, trimethylsilyl (TMS), t-butyldimethylsilyl (TBS or TBDMS), t-butyldiphenylsilyl (TBDPS), t-butoxycarbonyl, trichloroethoxycarbonyl, acetyl, pivaloyl and the like.

The adjacent hydroxyl groups may be protected as acetal or silylacetal.

As a starting compound, unless particularly indicated, a commercially available product can be obtained easily, or can be produced according to a method known per se or a method analogous thereto.

In each reaction to synthesize respective reaction and starting compounds, a generally-known solvent may be used in the reaction. Examples of the generally-known solvent include aliphatic hydrocarbons such as hexane, heptane, ligroin, petroleum ether; aromatic hydrocarbons such as benzene, toluene, xylene; hydrocarbon halides such as methylene chloride, chloroform, carbon tetrachloride, dichloroethane, chlorobenzene, dichlorobenzene; esters such as ethyl formate, ethyl acetate, propyl acetate, butyl acetate, diethyl carbonate; ethers such as diethyl ether, diisopropyl ether, tetrahydrofuran, dioxane, dimethoxyethane, diethylene glycol dimethylether; alcohols such as methanol, ethanol, n-propanol, isopropanol, n-butanol, isobutanol, t-butanol, isoamylalcohol, diethylene glycol, glycerol, octanol, cyclohexanol, methylcellosolve; ketones such as acetone, methylethyl ketone, methyl isobutyl ketone, isophorone, cyclohexanone; nitro compounds such as nitroethane, nitrobenzene; nitriles such as acetonitrile, isobutyronitrile; amides such as formamide, dimethylformamide, dimethylacetamide, hexamethylphosphorotriamide; sulfoxides such as dimethyl sulfoxide and mixed solvents of these and water.

The solvent used in the reaction may be a single solvent or a mixture of 2 to 6 kinds of solvents may be used.

The reaction may be performed in the co-presence of, for example, amines such as triethylamine, N,N-diisopropylamine, pyridine, N-methylmorpholine and the like, or bases such as sodium hydroxide, potassium carbonate and the like.

The reaction may be performed in the co-presence of, for example, acids such as hydrochloric acid, sulfuric acid, acetic acid and the like.

The synthesis Schemes of the compound of the present invention are shown below (detailed reactions follow Examples). In the Schemes, specific groups and compounds are sometimes used for description. However, it is clear to those of ordinary skill in the art that alternative groups and compounds can be used.

Scheme 1

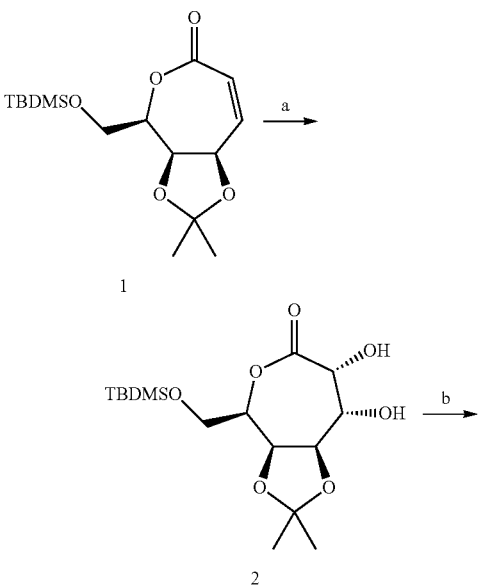

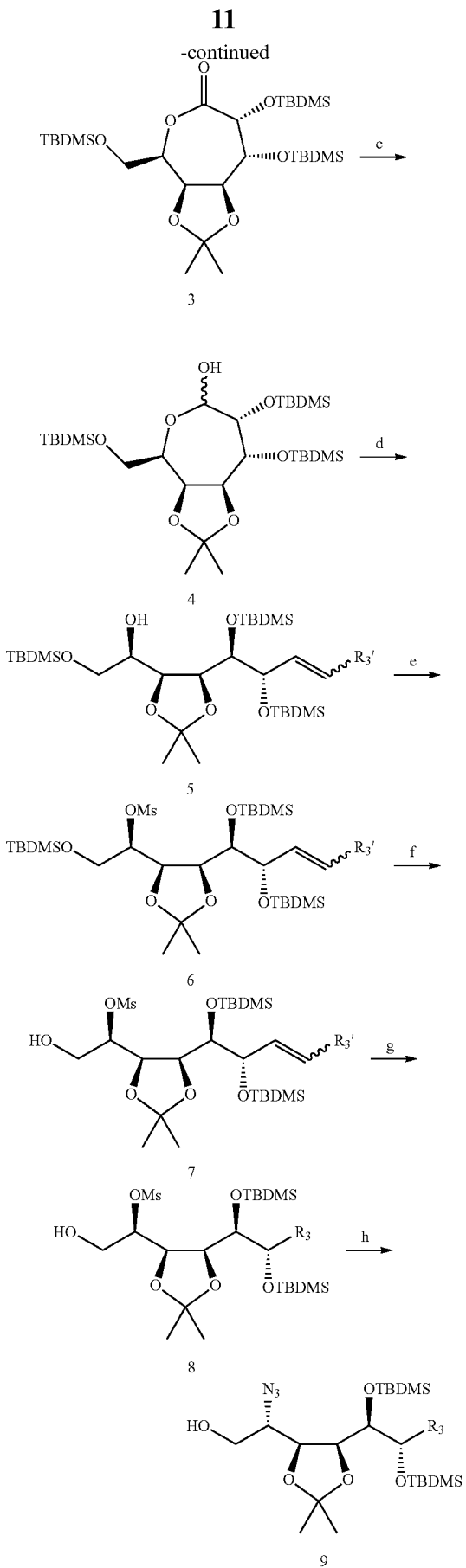

In each formula, TBDMS is a t-butyldimethylsilyl group, Ms is a mesyl group, $R_3'$ is $R_3$ with a carbon number smaller by 2, and other symbols are as defined above.

[Step a]

In Step a, compound 2 is obtained by introducing a hydroxyl group into the double bond of compound 1 (diol reaction). To be specific, compound 1 is reacted with a catalytic amount of osmium tetraoxide and an oxidant such as N-methylmorpholine N-oxide and the like in a solvent in the presence of an acid. As the acid, strong acids such as trifluoroacetic acid, p-toluenesulfonic acid, hydrochloric acid and the like can be used, and preferred is p-toluenesulfonic acid. As the solvent, any solvent can be used as long as it does not inhibit this reaction, and preferred is a mixed solvent of acetone and water.

The amount of the oxidant to be used is generally 1-10 equivalents relative to compound 1. The amount of the acid to be used is generally 1-10 equivalents relative to compound 1. The amount of the solvent to be used is generally 10- to 100-fold volume relative to compound 1.

The reaction temperature is generally 0° C.—room temperature, and the reaction time is generally 1-24 hr.

Compound 1 can be synthesized by a method known in a document (Tetrahedron, 63, 4310-4318 (2007)).

[Step b]

In Step b, the hydroxyl group of compound 2 is protected to give compound 3. To be specific, compound 2 is reacted with a protecting reagent in a solvent in the presence of a base. Bases include amino compounds such as pyridine, 2,6-lutidine, triethylamine and the like, with preference given to 2,6-lutidine. As the protecting reagent, an organic silicon reagent is preferable, and tert-butyldimethylsilyl trifluoromethanesulfonate (TBDMSOTf), tert-butyldimethylsilyl chloride and the like can be mentioned, with preference given to TBDMSOTf. As the solvent, any solvent can be used as long as it does not inhibit this reaction, and preferred is methylene chloride.

The amount of the base to be used is generally 1-10 equivalents relative to compound 2. The amount of the protecting reagent to be used is generally 1-5 equivalents per one hydroxyl group of compound 2. The amount of the solvent to be used is generally 10- to 100-fold volume relative to compound 2.

The reaction temperature is generally 0° C.—room temperature, and the reaction time is generally 1-24 hr.

[Step c]

In Step c, compound 4 is obtained by reducing ketone of compound 3. To be specific, compound 3 is reacted with a reducing agent in a solvent. Examples of the reducing agents include lithium aluminum hydride (LiAlH$_4$), sodium borohydride (NaBH$_4$), diisobutylaluminum hydride (DIBAH) and the like, and preferred is DIBAH. As the solvent, any solvent can be used as long as it does not inhibit this reaction, and preferred is toluene.

The amount of the reducing agent to be used is generally 1-10 equivalents relative to compound 3. The amount of the solvent to be used is generally 10- to 100-fold volume relative to compound 3.

The reaction temperature is generally −78° C.—room temperature, and the reaction time is generally 0.1-24 hr.

[Step d]

In Step d, compound 5 is obtained by cleaving the ring of compound 4 and introducing a hydrocarbon group. To be specific, for example, when the hydrocarbon group to be introduced is an alkyl group, compound 4 is reacted with alkyl-triphenylphosphoniumhalide (preferably bromide) and a base [for example, lithium bis(trimethylsilyl)amide (LiN (TMS)$_2$)], and the obtained phosphorane is subjected to the Wittig reaction to give compound 5. The halogenated hydrocarbon group can be appropriately selected according to the hydrocarbon group to be introduced. As the solvent, any solvent can be used as long as it does not inhibit this reaction, and preferred is THF.

The amount of alkyl-triphenylphosphonium halide to be used is generally 2-4 equivalents relative to compound 4. The amount of the solvent to be used is generally 10- to 100-fold volume relative to compound 4.

The reaction temperature is generally −78° C.—room temperature, and the reaction time is generally 0.1-24 hr.

[Step e]

In Step e, compound 6 is obtained by mesylating the hydroxyl group of compound 5. To be specific, compound 5 is reacted with a mesylating agent in a solvent in the presence of a base. Bases include triethylamine, pyridine, dimethylaminopyridine and the like, and preferred is pyridine. As the mesylating agent, methanesulfonic anhydride, methanesulfonyl chloride, methanesulfonyl fluoride and the like can be mentioned, and preferred is methanesulfonic anhydride. As the solvent, any solvent can be used as long as it does not inhibit this reaction, and preferred is methylene chloride.

The amount of the base to be used is generally catalytic amount—5 equivalents relative to compound 5. The amount of the mesylating agent to be used is generally 1-10 equivalents relative to compound 5. The amount of the solvent to be used is generally 10- to 100-fold volume relative to compound 5.

The reaction temperature is generally 0° C.—room temperature, and the reaction time is generally 0.1-24 hr.

[Step f]

In Step f, compound 7 is obtained by deprotecting a part of the hydroxyl group of compound 6. The deprotection method is selected from known methods according to the kind of the protecting group. For example, when protecting group is a TBDMS group, only the C$_1$-position primary TBDMS group needs to selectively deprotected, and a strong acid cannot be used. Therefore, hydrogen fluoride-pyridine or tetrabutylammoniumfluoride (TBAF) is used for compound 6 in a solvent. Preferred is hydrogen fluoride-pyridine. As the solvent, a mixed solvent of tetrahydrofuran and pyridine is preferable.

The amount of hydrogen fluoride-pyridine to be used is generally catalytic amount—10 equivalents, preferably 1-2 equivalents, relative to compound 6. The amount of the tetrabutylammoniumfluoride to be used is generally 2 equivalents—20 equivalents relative to compound 6. The amount of the solvent to be used is generally 1- to 100-fold volume relative to compound 6.

The reaction temperature is generally −20-60° C., and the reaction time is generally 1-24 hr.

[Step g]

In Step g, compound 8 is obtained by reducing the double bond in compound 7. To be specific, compound 7 is reacted in a solvent in the presence of hydrogen and a reduction catalyst. As the solvent, any solvent can be used as long as it does not inhibit this reaction, and preferred is hexane or ethyl acetate. As the reduction catalyst, palladium-carbon, palladium hydroxide, palladium hydroxide-activated carbon, platinum oxide, Raney-nickel and the like can be mentioned, and preferred is palladium-carbon.

The amount of the solvent to be used is generally 10- to 100-fold volume relative to compound 7. As the amount of the reduction catalyst, a catalytic amount for compound 7 is generally sufficient.

The reaction temperature is generally 0° C.—room temperature, and the reaction time is generally 0.1-24 hr.

[Step h]

In Step h, compound 9 is obtained by azidizing the methanesulfonyloxy group (OMs) in compound 8 to convert same to N$_3$ to give compound 9. For azide reaction, sodium azide is generally used, and the amount of use thereof is generally 5-20 equivalents relative to compound 8.

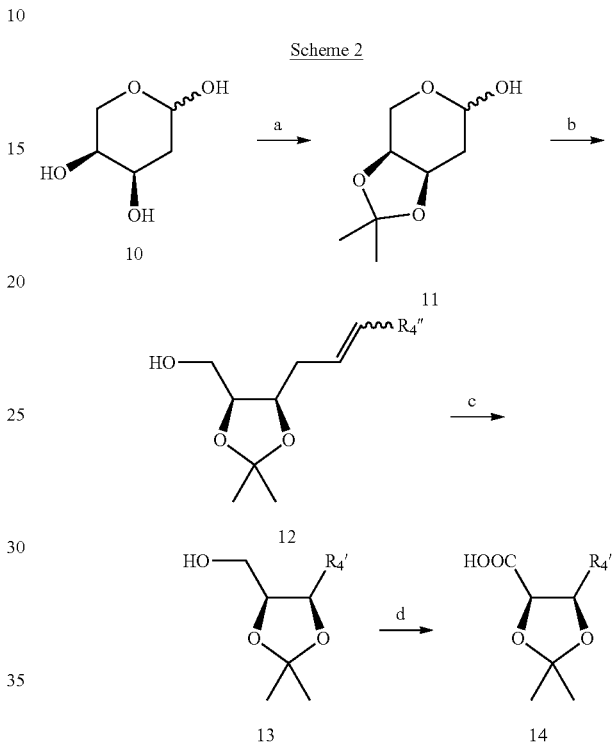

Scheme 2

In each formula, R$_4$' is R$_4$ with a carbon number higher by 1, R$_4$" is R$_4$ with a carbon number smaller by 2, and R$_4$ is as defined above.

[Step a]

In Step a, compound 11 is obtained by subjecting compound 10 to an isopropylidenation reaction. The isopropylidenation reaction is performed by reacting compound 10 with 2,2-dimethoxypropane in a solvent. As the solvent, any solvent can be used as long as it does not inhibit this reaction, and preferred is DMF.

Said reaction may be performed in the presence of an acid catalyst. Acid catalysts include inorganic acids such as hydrochloric acid, sulfuric acid and the like, organic acids such as methanesulfonic acid, p-toluenesulfonic acid and the like, and ion exchange resin (H$^+$ type).

The amount of 2,2-dimethoxypropane to be used is generally 1-10 equivalents relative to compound 10. The amount of the acid catalyst to be used is generally 0.01-1 equivalent relative to compound 10. The amount of the solvent to be used is generally 10- to 100-fold volume relative to compound 10.

The reaction temperature is generally room temperature −100° C. The reaction time is generally 0.5-24 hr.

Compound 10 can be synthesized by a method known in a document or is also commercially available.

[Step b]

In Step b, compound 12 is obtained by cleaving the ring of compound 11 and introducing a hydrocarbon group. To be specific, for example, when the hydrocarbon group to be introduced is an alkyl group, compound 11 is reacted with alkyl-triphenylphosphoniumhalide (preferably bromide) and a base [for example, lithium bis(trimethylsilyl)amide (LiN(TMS)$_2$)], and subjected to the Wittig reaction with the obtained phosphorane to give compound 12. The halogenated hydrocarbon group can be appropriately selected according to the hydrocarbon group to be introduced. As the solvent, any solvent can be used as long as it does not inhibit this reaction, and preferred is THF.

The amount of alkyl-triphenylphosphoniumhalide to be used is generally 2-4 equivalents relative to compound 11. The amount of the solvent to be used is generally 10- to 100-fold volume relative to compound 11.

The reaction temperature is generally −78° C.—room temperature, and the reaction time is generally 1-24 hr.

[Step c]

In Step c, compound 13 is obtained by reducing the double bond in compound 12. This step can be performed in the same manner as in Scheme 1, step g.

[Step d]

In Step d, compound 14 is obtained by oxidizing the hydroxyl group of compound 13 to a carboxyl group. To be specific, compound 13 is reacted with a catalytic amount of an oxidant in the presence of excess sodium periodate in a solvent. Oxidants include ruthenium tetroxide, ruthenium dioxide, ruthenium trichloride and hydrates thereof, ruthenium compounds such as ruthenium-phosphine complex, ruthenium-carbon monoxide complex and the like, and preferred are ruthenium trichloride and a hydrate thereof. As the solvent, any solvent can be used as long as it does not inhibit this reaction, and preferred is a mixed solvent of carbon tetrachloride, acetonitrile and water.

The amount of the oxidant to be used is generally catalytic amount—1 equivalent relative to compound 13. The amount of the solvent to be used is generally 10- to 100-fold volume relative to compound 13.

The reaction temperature is generally 0° C.—room temperature, and the reaction time is generally 0.1-24 hr.

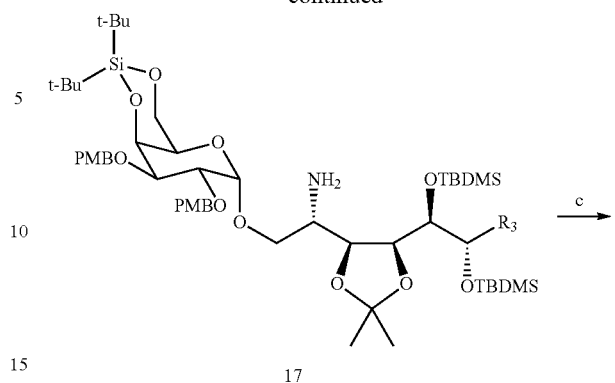

17

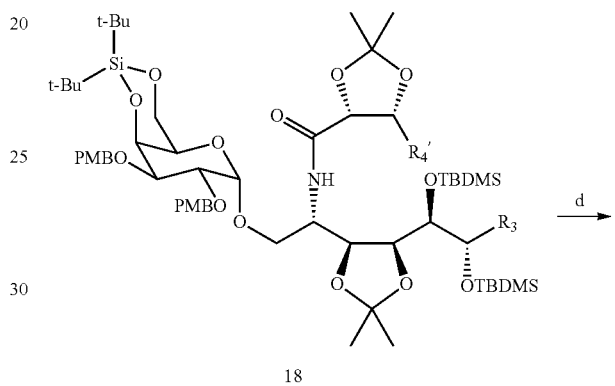

18

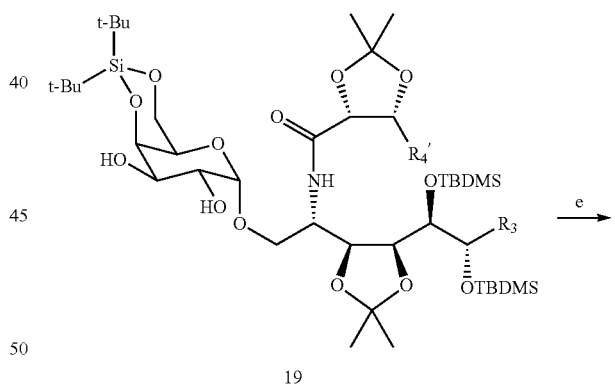

19

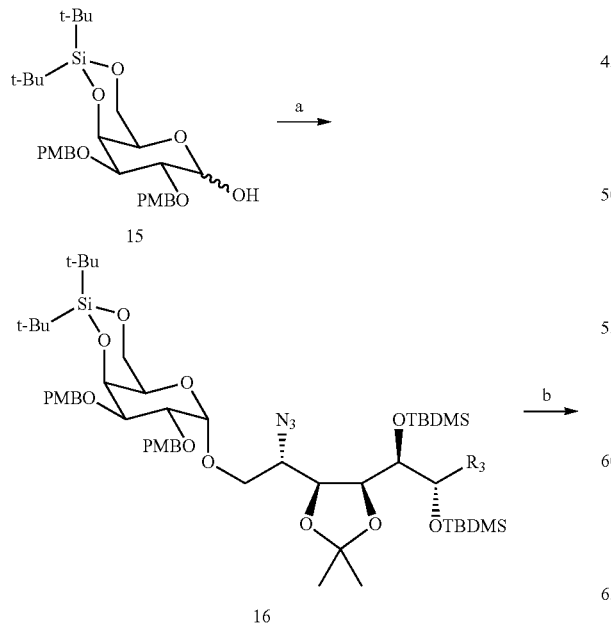

Scheme 3

15

16

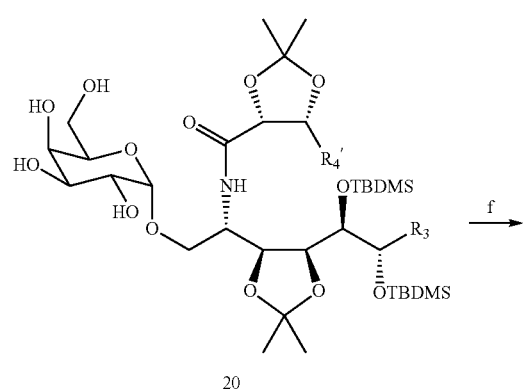

20

-continued

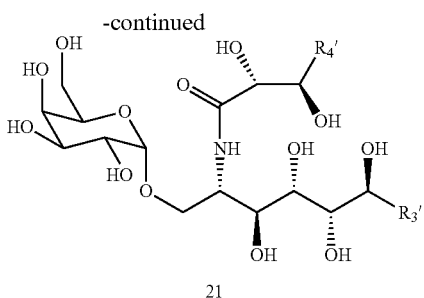

21

In each formula, each symbol is as defined above.

[Step a]

In Step a, compound 16 is obtained by reacting compound 15 with compound 9 by using trimethylsilyl trifluoromethanesulfonate or silvertrifluoromethanesulfonate as a catalyst in a solvent in the presence of molecular sieves. The starting compound 15 can be synthesized by a method known in a document (Carbohydr. Res. 345, 1663-1684 (2010)).

Compound 15 needs to be converted to an imidate form before reaction with compound 9.

The amount of compound 15 to be used is generally 0.1-10 equivalents relative to compound 9. The amount of trifluoromethanesulfonate to be used is generally 0.01-3 equivalents relative to compound 15. The amount of the molecular sieve to be used is generally 1-2 g relative to 1 mmol of compound 15. The amount of the solvent to be used is generally 10- to 100-fold volume relative to compound 15.

The reaction temperature is generally 0° C.—room temperature, and the reaction time is generally 0.1-24 hr.

[Step b]

In Step b, compound 17 is obtained by reducing the azide group of compound 16 to an amino group. To be specific, compound 16 is reacted with a reducing agent in a solvent. Reducing agents include catalytic hydrogenation reducing catalysts such as trimethylphosphine, tributylphosphine, triphenylphosphine, hydrogen and palladium-carbon, palladium black, palladium hydroxide, platinum oxide and the like, and the like. Preferable reaction includes converting to iminophosphorane (—N=PMe$_3$) with trimethylphosphine in THF, and hydrolyzing P=N double bond with aqueous sodium hydroxide solution to give amine 17. As the solvent, any solvent can be used as long as it does not inhibit this reaction, and methanol, ethanol, THF, dioxane, DMF, water, a mixed solvent of these organic solvents and water, and the like can be mentioned, with preference given to THF.

The amount of the reducing agent to be used is generally 1-10 equivalents relative to compound 16. The amount of the solvent to be used is generally 10- to 100-fold volume relative to compound 16.

The reaction temperature is generally 10-30° C., and the reaction time is generally 0.5-8 hr.

[Step c]

In Step c, compound 18 is obtained by dehydration condensation of amine of compound 17 and carboxylic acid of compound 14. To be specific, compound 17 is reacted with compound 14 in a solvent in the presence of a condensing agent. 1-Hydroxybenzotriazole (HOBt) or DMAP are added where necessary.

As the condensing agent, water-soluble carbodiimide, particularly, 1-ethyl-3-(3-dimethylaminopropyl)carbodiimide hydrochloride is preferably used. As the solvent, any solvent can be used as long as it does not inhibit this reaction, and THF and methylene chloride can be mentioned. Preferred is a mixed solvent of THF and methylene chloride.

The amount of compound 14 to be used is generally 1-5 equivalents relative to compound 17. The amount of the condensing agent to be used is generally 1-20 equivalents relative to compound 17. When HOBt or DMAP are added, the amount thereof to be used is generally 5-20 equivalents relative to compound 17. The amount of the solvent to be used is generally 10- to 100-fold volume relative to compound 17.

The reaction temperature is generally 10-30° C., and the reaction time is generally 0.5-24 hr.

[Step d]

In Step d, compound 19 is obtained by deprotecting the hydroxyl-protecting group of compound 18. The deprotection method is selected from known methods according to the kind of the protecting group. For example, when the protecting group is a PMB group, compound 18 is reacted with a deprotecting agent which is an oxidant such as 2,3-dichloro-5,6-dicyano-1,4-benzoquinone (DDQ) and the like in a solvent. As the solvent, a mixed solvent of hydrocarbon halide such as methylene chloride and the like and water is preferably used.

The amount of the deprotecting agent to be used is generally 1-10 equivalents relative to compound 18. The amount of the solvent to be used is generally 10- to 100-fold volume relative to compound 18.

The reaction temperature is generally −20° C.-100° C., and the reaction time is generally 0.5-20 hr.

[Step e]

In Step e, compound 20 is obtained by deprotecting the hydroxyl-protecting group of compound 19. The deprotection method is selected from known methods according to the kind of the protecting group. For example, when a protecting group having a silylacetal structure such as a di-(t-butyl)-silylene group (DTBS group) and the like is formed cyclic over two hydroxyl groups on the sugar structure, compound 19 is reacted with a deprotecting agent such as HF-pyridine, tetrabutylammonium fluoride (TBAF), hydrofluoric acid (HF), cesium fluoride (CsF) and the like in a solvent. As the solvent, any solvent can be used as long as it does not inhibit this reaction, and preferred is THF, pyridine or a mixed solvent of THF and pyridine.

The amount of the deprotecting agent to be used is generally 0.5-20 equivalents relative to compound 19. The amount of the solvent to be used is generally 10- to 100-fold volume relative to compound 19.

The reaction temperature is generally 10° C.—room temperature, and the reaction time is generally 1-5 hr.

[Step f]

In Step f, compound 21 is obtained by deprotecting the isopropylidene group and TBDMS group as hydroxyl-protecting groups in compound 20. To be specific, compound 20 is reacted with a deprotecting agent such as hydrofluoric acid (HF), hydrochloric acid, p-toluenesulfonic acid, acetic acid water, and the like in a solvent. As the solvent, any solvent can be used as long as it does not inhibit this reaction, and a mixed solvent of methylene chloride and acetonitrile is preferably used.

The amount of the deprotecting agent to be used is generally 0.5-20 equivalents relative to compound 20. The amount of the solvent to be used is generally 50- to 500-fold volume relative to compound 20.

The reaction temperature is generally 10° C.—room temperature, and the reaction time is generally 0.1-24 hr.

Scheme 4

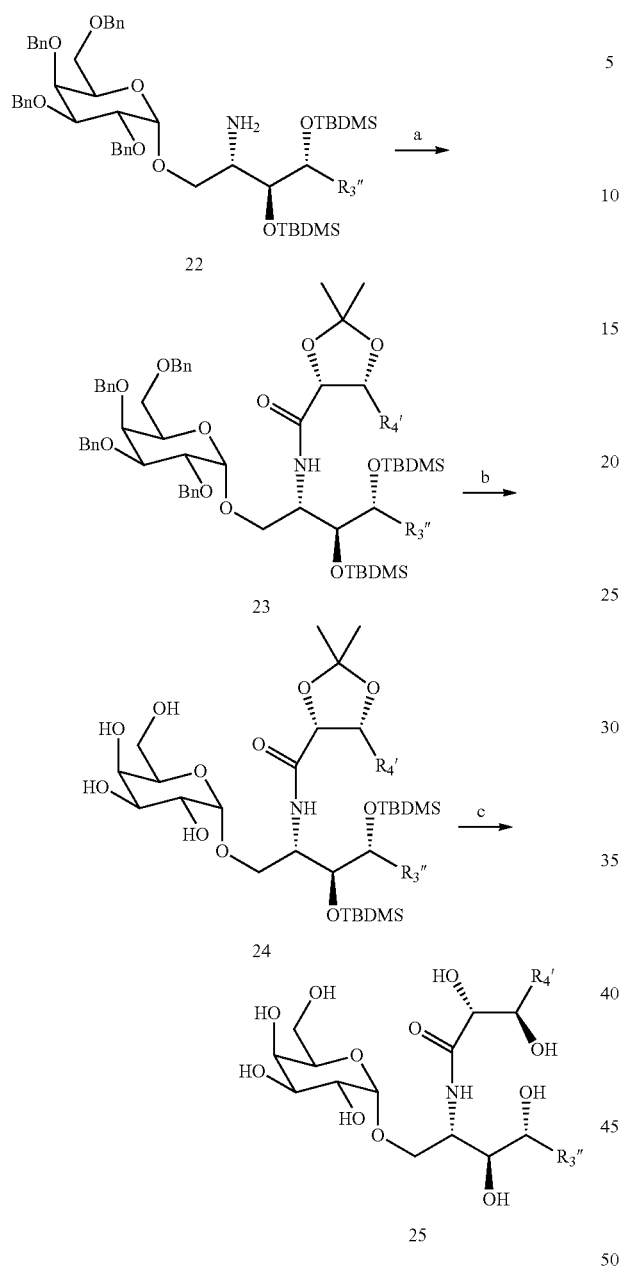

In each formula, $R_3''$ is $R_3$ with a carbon number higher by 2, and $R_3$ is as defined above.

[Step a]

In Step a, compound 23 is obtained by dehydration condensation of amine of compound 22 and carboxylic acid of compound 14. This step can be performed in the same manner as in Scheme 3, step c, except that compound 22 is used instead of compound 17. The starting compound 22 can be synthesized by a method known in a document (Bioorg. & Med. Chem. 2008, 16, 8896-8906).

[Step b]

In Step b, compound 24 is obtained by deprotecting the hydroxyl-protecting group of compound 23. The deprotection method is selected from known methods according to the kind of the protecting group. For example, in the case of a benzyl group, compound 23 is reacted in a solvent in the presence of hydrogen and a reduction catalyst. Examples of the reduction catalyst include palladium hydroxide, palladium hydroxide-activated carbon, platinum oxide, Raney-nickel and the like. As the solvent, methanol, ethanol, chloroform, ethyl acetate, acetic acid and THF are preferably used.

As the amount of the reduction catalyst to be used, a catalytic amount relative to compound 23 is generally sufficient. The amount of the solvent to be used is generally 10- to 100-fold volume relative to compound 23.

The reaction temperature is generally at room temperature, and the reaction time is generally 1-24 hr.

[Step c]

In Step c, compound 25 is obtained by deprotecting isopropylidene group and TBDMS group as hydroxyl-protecting groups in compound 24. This step can be performed in the same manner as in Scheme 3, step f.

Scheme 5

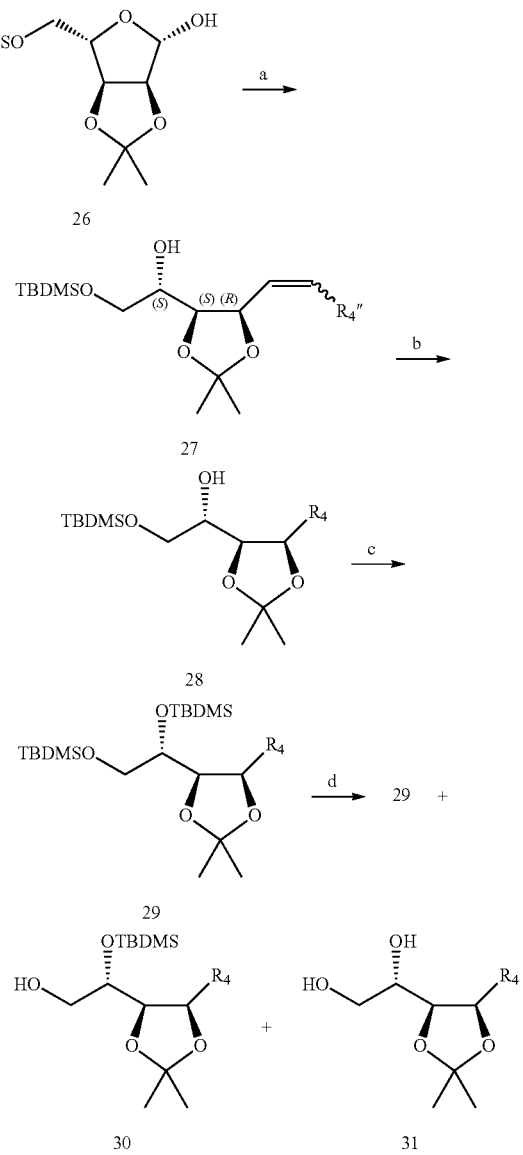

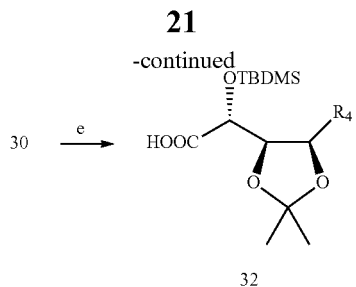

In each formula, each symbol is as defined above.

[Step a]

In Step a, compound 27 is obtained by cleaving the ring of compound 26 and introduction of a hydrocarbon group. To be specific, for example, when the hydrocarbon group to be introduced is an alkyl group, compound 26 is subjected to the Wittig reaction with phosphorane obtained by reacting alkyl-triphenylphosphonium halide (preferably bromide) and a base [e.g., n-butyllithium (n-BuLi)]. The halogenated hydrocarbon group can be appropriately selected according to the hydrocarbon group to be introduced. As the solvent, any solvent can be used as long as it does not inhibit this reaction.

The amount of alkyl-triphenylphosphoniumhalide to be used is generally 2-4 equivalents relative to compound 26. The amount of the solvent to be used is generally 10- to 100-fold volume relative to compound 26.

The reaction temperature is generally −78° C.—room temperature, and the reaction time is generally 0.1-24 hr.

The starting compound 26 can also be synthesized by a method known in a document.

[Step b]

In Step b, compound 28 is obtained by reducing a double bond in compound 27. This step can be performed in the same manner as in Scheme 1, step g.

[Step c]

In Step c, compound 29 is obtained by protecting the hydroxyl group of compound 28. This step can be performed in the same manner as in Scheme 1, step b.

[Step d]

In Step d, compound 30 is obtained by selective deprotection of the hydroxyl group at the $C_1$-position of compound 29. To be specific, compound 29 is reacted with a deprotecting agent such as tetrabutylammonium fluoride (TBAF), hydrofluoric acid (HF)-pyridine, cesium fluoride (CsF) and the like in a solvent. The deprotecting agent is preferably HF-pyridine. As the solvent, a mixed solvent of pyridine and THF is preferably used.

The amount of the deprotecting agent to be used is generally 0.5-20 equivalents relative to compound 29. The amount of the solvent to be used is generally 10- to 100-fold volume relative to compound 29.

The reaction temperature is generally 10° C.—room temperature, and the reaction time is generally 0.1-24 hr.

After completion of the reaction, the reaction mixture is concentrated under reduced pressure, and the residue is purified by column chromatography, whereby compound 29, compound 30 and compound 31, which are starting compounds, can be isolated.

[Step e]

In Step e, compound 32 is obtained by oxidizing the hydroxyl group of compound 30 into a carboxyl group. This step can be performed in the same manner as in Scheme 2, step d.

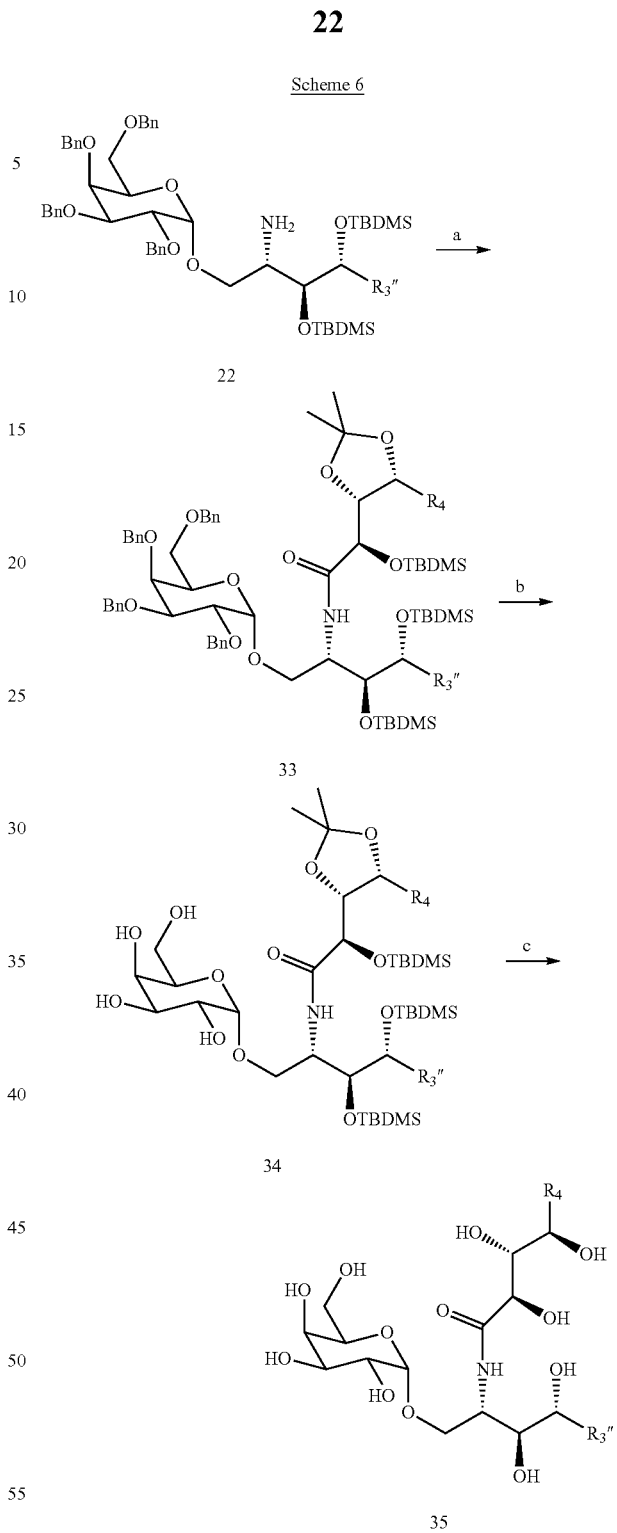

In each formula, each symbol is as defined above.

[Step a]

In Step a, compound 33 is obtained by dehydration condensation of amine of compound 22 and carboxylic acid of compound 32. This step can be performed in the same manner as in Scheme 4, step a.

[Step b]

In Step b, compound 34 is obtained by hydroxyl-protecting group of compound 33 and then deprotected to give compound 34. This step can be performed in the same manner as in Scheme 4, step b.

[Step c]

In Step c, compound 35 is obtained by deprotecting isopropylidene group and TBDMS group as hydroxyl-protecting groups in compound 34. This step can be performed in the same manner as in Scheme 4, step c.

By administering a compound represented by the formula (I) of the present invention (compound (1), hereinafter to be also referred to as hydroxylated glycolipid of the present invention"), NKT cell can be activated, and Th2 type cytokine can be selectively and preferentially induced.

By pulsing human dendritic cells with the hydroxylated glycolipid of the present invention and administering the dendritic cells to a subject, a stronger Th2 type cytokine production inducing action can be obtained. The human dendritic cell used here is not particularly limited as long as it is a human-derived dendritic cell (hDC) capable of activating NKT cells via the hydroxylated glycolipid of the present invention, and may be any of myeloid dendritic cell (DC1) and lymphoid dendritic cell (DC2), with preference given to DC1. hDC may be prepared by any method known per se, and can also be separated from human epidermis, T cells region of lymphoid tissue, peripheral non-lymphoid tissue, afferent lymph, corium and the like. Preferably, it can be prepared by, for example, separating monocyte, myelocyte and the like from human peripheral blood and the like by a density gradient centrifugation method and the like, and culturing same for about 7-about 10 days in the presence of GM-CSF and IL-4.

hDC can be pulsed with the hydroxylated glycolipid of the present invention by a well-known conventional method. For example, hDC can be pulsed by being cultivated in a medium (e.g., RPMI-1640 medium etc.) containing the hydroxylated glycolipid of the present invention at a concentration of about 100-about 200 ng/ml for about 12-about 48 hr. The pulsing may also be performed by adding the glycolipid of the present invention to the medium in the process of culturing and maturing the above-mentioned immature hDC in the presence of GM-CSF and IL-4.

While the presence or absence of activation of NKT cells and the level thereof can be measured by any method known per se. For example, activation of NKT cells can be evaluated by using the amount of cytokine produced by activated NKT cells as an index. As the cytokine produced by activated NKT cells, IFN-γ, IL-4, GM-CSF, IL-10 and the like can be mentioned. The hydroxylated glycolipid of the present invention selectively induces production of Th2 type cytokine (e.g., IL-4). Preferable examples of the hydroxylated glycolipid of the present invention not only show cytokine secretion biased to the Th2 type, but also do not promote production of Th1 type cytokine (e.g., IFN-γ).

The production of cytokine by NKT cells can be measured by, for example, using an antibody to the cytokine. For example, activation of NKT cells can also be evaluated by a conventional immunoassay such as ELISA method, RIA method, FIA method, EIA method and the like and by using the cell culture supernatant. In a preferable embodiment, a method including contacting an NKT cell-containing sample with a solid phase immobilized with an anti-cytokine antibody and, after solid-liquid separation, detecting and counting cytokines bond to the solid phase by a sandwich method by using a labeled anti-cytokine antibody. Examples of the label include enzyme, fluorescent substance, luminescence substance, dye, radioisotope and the like. A biotinylated anti-cytokine antibody and label-bound (strept)avidin may also be used. An assay system using enzymes such as alkaline phosphatase and the like as a label is known by the name of ELISPOT for the detection of cytokine-producing cells.

The diseases that can be prevented or treated by the hydroxylated glycolipid of the present invention are not particularly limited as long as increase of IL-4 production is expected to show a direct or indirect prophylactic or therapeutic effect thereon. For example, autoimmune diseases, allergy and the like in mammals (e.g., mouse, cat, bovine, dog, horse, goat, monkey, human) can be mentioned. As the autoimmune disease, systemic lupus erythematosus, rheumatoid arthritis, type 1 and type 2 diabetes, inflammatory bowel disease, bile cirrhosis, uveitis, multiple sclerosis, as well as Crohn's disease, ulcerative colitis, bullous pemphigus, sarcoidosis, psoriasis, ichthyosis, Graves ophthalmic diseases, and asthma and the like can be mentioned. Furthermore, since the hydroxylated glycolipid can suppress excess immune responses in organ transplantation such as rejection and the like, it can also be used as an immunosuppressant.

In addition, as long as the efficacy is not impaired, the hydroxylated glycolipid of the present invention can be used in combination with other medicaments, for example, existing therapeutic drugs for autoimmune diseases, antiallergic agent, immunosuppressant and the like. In this case, the period for administration is not limited and these agents may be administered to the subject simultaneously or in time intervals. The dose can be appropriately determined by taking into account the clinically adopted dose as a standard. The mixing ratio of the hydroxylated glycolipid of the present invention to the concomitant drug may be appropriately determined depending on the administration subject, administration route, target disease, conditions, combination, and the like.

Examples of the existing therapeutic drug for autoimmune disease and/or immunosuppressant include steroids such as prednisolone and the like, gold drugs such as gold sodium thiomalate, auranofin and the like, SH preparations such as D-penicillamine, bucillamine and the like, salazosulfapyridine, actarit, lobenzarit sodium and the like. In addition, immunosuppressants such as mizoribine, methotrexate, cyclophosphamide, azathiopurine, FK-506, leflunomide and the like, anti-cytokine therapeutic agents such as anti-TNF-α antibody, soluble TNF-α receptor, anti-IL-6 antibody, IL-6 receptor antibody and the like, and the like can be mentioned.

Examples of the antiallergic agent include astemizole, amlexanox, ibudilast, ebastine, azelastine hydrochloride, epinastine hydrochloride, ozagrel hydrochloride, cetirizine hydrochloride, oxatomide, sodium cromoglycate, seratrodast, tazanolast, terfenadine, splatast tosilate, tranilast, emedastine fumarate, ketotifen fumarate, pranlukast hydrate, pemirolast potassium, repirinast etc., derivatives thereof and the like can be mentioned.

When the hydroxylated glycolipid of the present invention is administered to a human, it can be safely administered orally or parenterally, as is or after being blended with a pharmacologically acceptable carrier, excipient, diluent and the like, in the form of pharmaceutical compositions such as oral preparations (e.g., powders, granules, tablets, capsules), parenteral preparations (e.g., injections), and suppositories (e.g., rectal suppositories, vaginal suppositories). These preparations can be produced by conventionally known methods.

Examples of the injection include subcutaneous injections, intravenous injections, intramuscular injections, intraperitoneal injections, drip infusions and the like. An injection can be prepared as an aqueous injection by treating the glycolipid of the present invention in the presence of a solubilizer (e.g., β-cyclodextrins), a dispersing agent (e.g., carboxymethylcellulose, sodium alginate), a preservative (e.g., methylparaben, propylparaben, benzyl alcohol, chlorobutanol), an isotonizing agent (e.g., sodium chloride, glycerol, sorbitol, glucose) and the like by a conventional method. An injection can also be prepared as an oily injection by dissolving, suspending or emulsifying the glycolipid of the present invention in a vegetable oil (e.g., olive oil, sesame oil, peanut oil, cottonseed oil, corn oil), propylene glycol and the like.

An oral preparation can also be produced by adding to the hydroxylated glycolipid of the present invention, for example, an excipient (e.g., lactose, saccharose, starch), a disintegrant (e.g., starch, calcium carbonate), a binder (e.g., starch, gum arabic, carboxymethylcellulose, polyvinylpyrrolidone, hydroxypropylcellulose) or a lubricant (e.g., talc, magnesium stearate, polyethyleneglycol) and the like as appropriate, compression molding the mixture, and then, as required, coating the mixture with hydroxypropylmethylcellulose and the like. A suppository can be produced by blending the compound (1) etc. with a non-irritant excipient (e.g., polyethylene glycol, glycerides of higher fatty acids).

The dose of the hydroxylated glycolipid of the present invention varies depending on the age, body weight, symptoms, dosage form, method of administration, duration of administration and the like; for example, for a patient (adult, weighing about 60 kg), a daily dose of 0.1 to 1 mg/kg, preferably 0.5 to 1 mg/kg, more preferably 0.8 to 1 mg/kg, is administered orally or parenterally in a single to several divided portions.

In an attempt to induce Th2 type cytokine production, it is also possible to pulse dendritic cells with the hydroxylated glycolipid of the present invention, and administer the dendritic cells to patients. Therefore, the present invention provides a selective Th2 type cytokine production inducer m (specifically IL-4 production inducer) containing dendritic cells pulsed with the hydroxylated glycolipid of the present invention.

The agent can be produced as an oral/parenteral preparation according to a conventional means, by mixing an effective amount of the above-mentioned hDC pulsed with the hydroxylated glycolipid of the present invention with a pharmaceutically acceptable carrier, and the like. The agent is generally produced as a parenteral preparation such as injection, suspension, drip infusion and the like. Examples of the pharmaceutically acceptable carrier that can be contained in the parenteral preparation include aqueous solutions for injection such as physiological saline, isotonic solution containing glucose and other auxiliary agents (e.g., D-sorbitol, D-mannitol, sodium chloride and the like) and the like. The agent of the present invention may be blended with, for example, buffering agent (e.g., phosphate buffer, sodium acetate buffer), soothing agent (e.g., benzalkonium chloride, procaine hydrochloride and the like), stabilizer (e.g., human serum albumin, polyethylene glycol and the like), preservative, antioxidant and the like. When the agent is formulated as an aqueous suspension, hDCs pulsed with the hydroxylated glycolipid of the present invention only needs to be suspended in the above-mentioned aqueous solution at about $5 \times 10^6$-about $1 \times 10^7$ cells/ml. Since the thus-obtained preparation is stable and of lower toxicity, it can be safely administered to human. While the subject of administration is preferably the patient him/herself the hDC derives from (i.e., autologous transplantation), the subject is not limited when it is a human predicted to have compatibility with the hDC to be administered. The administration method is not particularly limited, and oral or parenteral administration can be employed. Preferred is injection or drip administration, and intravenous administration, subcutaneous administration, intradermal administration, intramuscular administration, intraperitoneal administration, direct administration to the affected part and the like can be mentioned. While the dose of the agent of the present invention varies depending on the subject of administration, target organ, symptom, administration method and the like, a single dose thereof is generally about $6 \times 10^5$-about $1 \times 10^7$ cells in the amount of hDC, which is, for example, conveniently administered parenterally to an adult patient (body weight 60 kg) about 4-about 8 times at about 1-about 2 weeks intervals.

EXAMPLES

The present invention is explained in more detail in the following by referring to Examples and Experimental Examples, which are not to be construed as limitative.

Example 1

Synthesis and Purification Method of RCAI-147

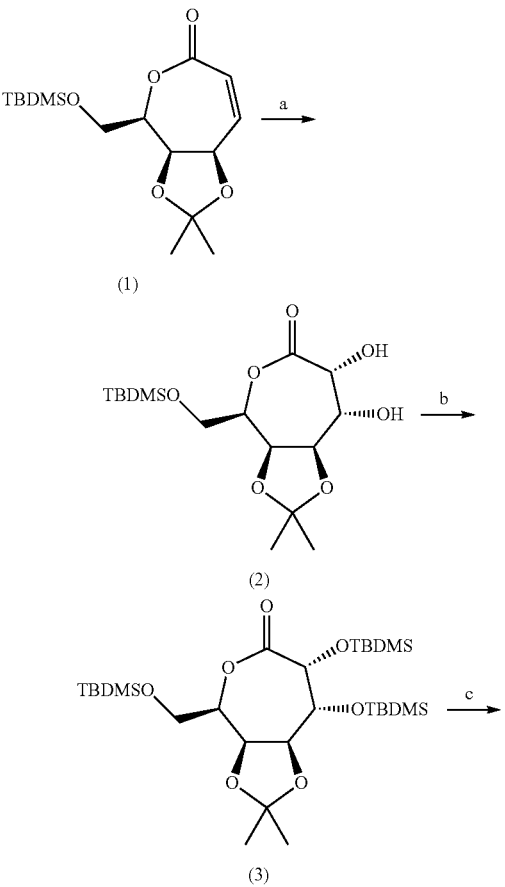

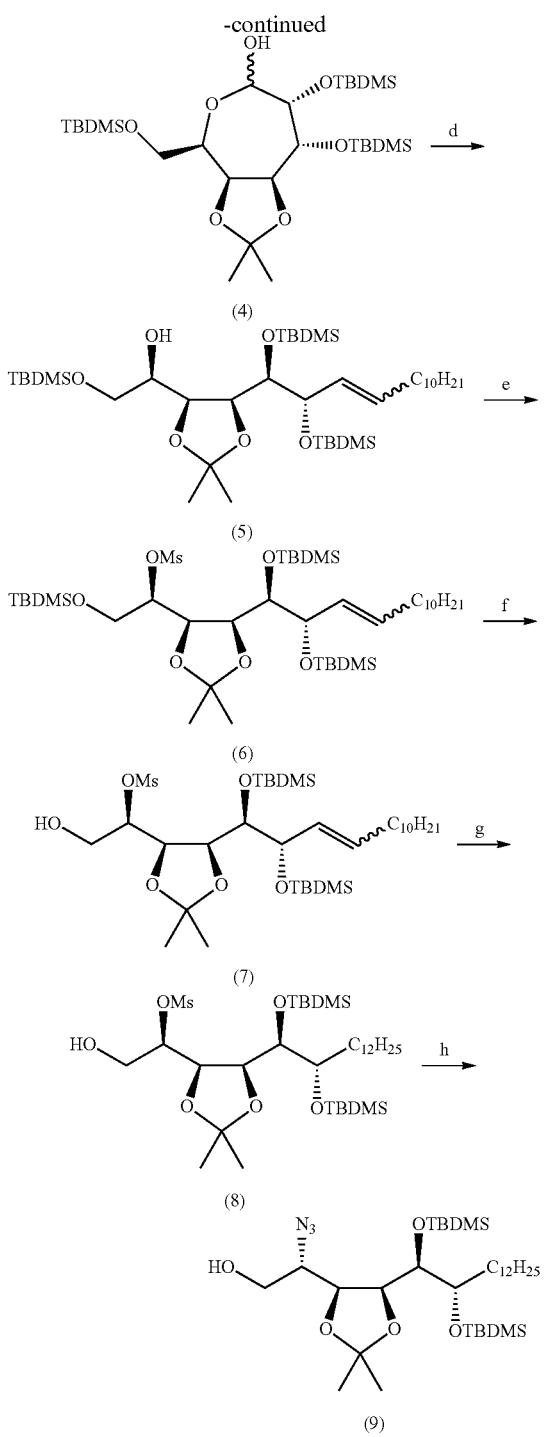

Step a: Synthesis of (3R,4S,5R,6S,7R)-7-[(tertiary butyldimethylsilyloxy)methyl]-5,6-O-isopropylidene-3,4-(dihydroxy)oxepan-2-one [compound (2)]

To a solution of compound (1) (3.00 g, 9.13 mmol) [C-W. Chang; Y-N. Chen; A. K. Adak; K-H. Lin; D-L. M. Tsou; C-C. Lin, Tetrahedron, 63, 4310-4318 (2007)], 4-methylmorpholine N-oxide (1.28 g, 11.0 mmol) and p-toluenesulfonic acid (2.07 g, 10.9 mmol) in acetone-H$_2$O (4:1, 150 mL) was added osmium tetraoxide (t-BuOH 1% solution, 30 mL) at 0° C., and the mixture was stirred at room temperature for 16 hr. The reaction solution was concentrated to half under reduced pressure at 25° C. The mixture was diluted with ethyl acetate (500 mL), washed with saturated brine and dried over magnesium sulfate. The residue was filtered, concentrated under reduced pressure, and purified by silica gel column chromatography. Elution thereof with hexane-ethyl acetate (4:1, further 2:1) gave compound (2) (2.10 g, 63%).

mp 107-108° C. (cotton-like, unstable at room temperature).

IR$v_{max}$(KBr) 3390 (br), 3000-2858, 1725, 1472 cm$^{-1}$.

$^1$H NMR (500 MHz, CDCl$_3$): δ0.089 (3H, s), 0.092 (3H, s), 0.90 (9H, s), 1.38 (3H, s), 1.50 (3H, s), 2.72 (1H, d, J 3.9 Hz, OH), 3.51 (1H, s, OH), 3.81 (1H, dd, J 9.3, 9.6 Hz), 3.94 (1H, dd, 5.6, 9.5 Hz), 4.24 (1H, m, changed to dd, J 1.5, 3.9 Hz, on addition of D$_2$O), 4.44 (1H, dd, J 4.3, 7.6 Hz), 4.52 (1H, bs, changed to doublet, J 1.5 Hz, on addition of D$_2$O), 4.70 (1H, d, J 7.6 Hz), 4.85 (1H, dd, J 5.6, 9.3 Hz).

FABMS: m/z 363.2 [M+H]$^+$.

HRFABMS: calcd for C$_{16}$H$_{31}$O$_7$Si: 363.1839; observed: 363.1853.

Step b: Synthesis of (3R,4R,5S,6S,7R)-7-[(tertiary butyldimethylsilyloxy)methyl]-5,6-O-isopropylidene-3,4-di(tertiary butyldimethylsilyloxy)oxepan-2-one [compound (3)]

To a solution of compound (2) (580 mg, 1.60 mmol) in 2,6-lutidine (1.72 g, 16.0 mmol)-containing CH$_2$Cl$_2$ (30 mL) was added tertiary butyldimethylsilyl trifluoromethanesulfonate (TBDMSOTf) (2.54 g, 9.60 mmol), and the mixture was stirred for 16 hr. The mixture was diluted with CH$_2$Cl$_2$, washed with water, and dried over magnesium sulfate. The residue was filtered, concentrated under reduced pressure, and purified by silica gel column chromatography. Elution thereof with hexane-ethyl acetate (9:1) gave compound (3) (908 mg, 96%).

IR$v_{max}$(KBr) 2990-2858, 1732, 1471, 1464 cm$^{-1}$.

$^1$H NMR (500 MHz, CDCl$_3$): δ0.07 (6H, s), 0.10 (3H, s), 0.11 (3H, s), 0.12 (3H, s), 0.14 (3H, s), 0.88 (9H, s), 0.89 (9H, s), 0.91 (9H, s), 1.36 (3H, s), 1.48 (3H, s), 3.80 (1H, dd, J 8.3, 9.8 Hz), 3.87 (1H, dd, J 6.2, 8.7 Hz), 3.88 (1H, d, J 6.4 Hz), 4.22 (1H, dd, J 6.4, 6.6 Hz), 4.49 (1H, d, J 1.0 Hz), 4.51 (1H, dd, J 1.0, 6.6 Hz), 5.14 (1H, dd, J 6.4, 8.3 Hz).

ESIMS: m/z 613.34 [M+Na]$^+$.

HRESIMS: calcd for C$_{28}$H$_{58}$O$_7$Si$_3$Na: 613.3383; observed: 613.3381.

Step c: Synthesis of (3R,4R,5S,6S,7R)-7-[(tertiary butyldimethylsilyloxy)methyl]-5,6-O-isopropylidene-3,4-di(tertiary butyldimethylsilyloxy)oxepan-2-ol [compound (4)]

To a solution of compound (3) (5.97 g, 10.1 mmol) in toluene (180 mL) was added diisobutylaluminum hydride (DIBAH) (toluene 1.0 M solution, 10.8 mL, 10.8 mmol) under an argon stream at −78° C. After stirring for 45 min, MeOH (15 mL) was added, and the mixture was further stirred at −78° C. for 30 min to complete the reaction. At room temperature, the mixture was diluted with ethyl acetate and washed with water. The organic layer was filtered through celite. The filtrate was dried over magnesium sulfate, filtered, concentrated under reduced pressure, and purified by silica gel column chromatography. Elution thereof with hexane-ethyl acetate (19:1, further 14:1) gave compound (4) (5.77 g, 96%) as an oily 2:1 anomer mixture.

IRν$_{max}$(KBr) 3440, 2954, 2930, 2887, 2858, 1748 (w), 1472, 1464, 1389, 1379, 1362, 1255 cm$^{-1}$.

$^1$H NMR (500 MHz, CDCl$_3$): δ0.05-0.06 (6H, m), 0.10-0.14 (12H, m), 0.87-0.93 (27H, m), 1.33 (2/3H, s), 1.34 (1/3H, s), 1.56 (3H, s), 2.63 (2/3H, d, J 4.2 Hz, OH), 3.68-3.74 (3H, m), 3.92-3.97 (1H, m), 4.22 (2/3H, m), 4.26-4.37 (2H, m), 4.55 (1/3H, m), 4.88 (2/3H, dd, J 4.4, 6.8 Hz, changed to doublet, J 6.8 Hz, on addition of D$_2$O), 5.06 (1/3H, m), 5.53 (1/3H, m, OH).

ESIMS: m/z 615.35 [M+Na]$^+$.

HRESIMS: calcd for C$_{28}$H$_{60}$O$_7$Si$_3$Na: 615.3539; observed: 615.3540.

Step d: Synthesis of (2R,3S,4S,5R,6S)-1,5,6-tri(tertiary butyldimethylsilyloxy)-3,4-O-isopropylideneoctade-7-cen-2-ol [compound (5)]

To a solution of n-C$_{11}$H$_{23}$P(Ph)$_3$Br (9.46 g, 19.0 mmol) in THF (47 mL) was added a solution of compound (4) (2.82 g, 4.76 mmol) in THF (23 mL) at −30° C. under an argon stream, and LiN(TMS)$_2$ (THF 1 M solution, 28 mL) was further added with stirring. Five min later, the mixture was warmed to −10° C. over 20 min. The mixture was stirred at this temperature for 15 min, and continuously stirred at room temperature for 3 hr. MeOH (4 mL) was added at 0° C., and the mixture was further diluted with ethyl acetate, washed with water and dried over magnesium sulfate. The residue was filtered, concentrated under reduced pressure, and purified by silica gel column chromatography. Elution thereof with hexane-ethyl acetate (40:1) gave compound (5) (1.88 g, 54%).

IRν$_{max}$(KBr) 3484, 2927, 2856 cm$^{-1}$.

$^1$H NMR (500 MHz, CDCl$_3$): δ0.03 (3H, s), 0.05 (3H, s), 0.07 (6H, s), 0.08 (3H, s), 0.09 (3H, s), 0.87-0.91 (30H, m, containing 9H singlet and 18H singlet at 0.87 and 0.90 ppm, respectively), 1.26-1.40 (19H, m, containing 3H singlet at 1.32 ppm), 1.48 (3H, s), 1.98 (1H, m), 2.06 (1H, m), 2.23 (1H, d, J 6.1 Hz, OH), 3.58 (1H, d, J 1.7 Hz), 3.59 (1H, s), 3.71 (1H, q, J 6.1 Hz), 3.99 (1H, dd, J 6.5, 9.7 Hz), 4.14 (1H, d, J 6.4 Hz), 4.23 (1H, dd, J 2.7, 9.8 Hz), 4.27 (1H, dd, J 2.6, 8.4 Hz), 5.44-5.53 (2H, m).

ESIMS: m/z 753.5 [M+Na]$^+$.

HRESIMS: calcd for C$_{39}$H$_{82}$O$_6$Si$_3$Na: 753.5311; observed: 753.5314.

Step e: Synthesis of (2R,3R,4S,5R,6S)-1,5,6-tri(tertiary butyldimethylsilyloxy)-3,4-O-isopropylidene-2-methanesulfonyloxyoctade-7-cene [compound (6)]

To a solution of compound (5) (840 mg, 1.15 mmol) in CH$_2$Cl$_2$ (40 mL) were added pyridine (4 mL) and methanesulfonic anhydride (840 mg, 4.82 mmol), and the mixture was stirred at room temperature for 45 min and diluted with CH$_2$Cl$_2$. The mixture was washed with saturated aqueous sodium hydrogen carbonate and dried over magnesium sulfate. The residue was filtered, concentrated under reduced pressure, and purified by silica gel column chromatography. Elution thereof with hexane-ethyl acetate (30:1) gave compound (6) (719 mg, 77%).

IRν$_{max}$(KBr) 2929, 2857, 1471, 1345, 1254, 1178 cm$^{-1}$.

$^1$H NMR (500 MHz, CDCl$_3$): δ0.04 (3H, s), 0.088 (6H, s), 0.093 (3H, s), 0.10 (3H, s), 0.11 (3H, s), 0.88 (9H, s), 0.89 (3H, m), 0.90 (9H, s), 0.91 (9H, s), 1.25-1.40 (19H, m, containing 3H singlet at 1.30 ppm), 1.45 (3H, s), 1.99 (1H, m), 3.08 (3H, s), 3.84 (1H, dd, J 7.5, 10.0 Hz), 3.97-4.02 (2H, m), 4.21 (1H, dd, J 2.2, 9.7 Hz), 4.25 (1H, d, J 6.1 Hz), 4.31 (1H, dd, J 2.2, 8.5 Hz), 4.77 (1H, t, J 6.5 Hz), 5.44-5.53 (2H, m). ESIMS: m/z 831.5 [M+Na]$^+$.

HRESIMS: calcd for C$_{40}$H$_{84}$O$_8$Si$_3$SNa: 831.5087; observed: 831.5088.

Step f: Synthesis of (2R,3R,4S,5R,6S)-5,6-di(tertiary butyldimethylsilyloxy)-3,4-O-isopropylidene-2-methanesulfonyloxyoctade-7-cen-1-ol [compound (7)]

To a solution of compound (6) (128 mg, 0.158 mmol) and pyridine (1.0 mL) in THF (1.7 mL) was added HF-pyridine (HF: up to 70%; pyridine: up to 30%, 0.34 mL) at 0° C. under an argon stream. Five minutes later, the mixture was stirred at room temperature for 5 hr. The mixture was diluted with ethyl acetate, washed with saturated aqueous sodium hydrogen carbonate and dried over magnesium sulfate. The residue was filtered, concentrated under reduced pressure, and purified by silica gel column chromatography. Elution thereof with hexane-ethyl acetate (9:1) gave compound (7) (68 mg, 62%) as an (E,Z) mixture with a double bond.

IRν$_{max}$(KBr) 3540, 2927, 2856, 1466, 1342, 1253 cm$^{-1}$.

$^1$H NMR (500 MHz, CDCl$_3$): δ0.05 (3H, s), 0.06 (3H, s), 0.07 (3H, s), 0.12 (3H, s), 0.88 (18H, s, and 3H, t, J 7.1 Hz), 1.25-1.40 (19H, m, containing 3H singlet at 1.33 ppm), 1.49 (3H, s), 2.02 (1H, m), 2.10 (1H, m), 2.87 (1H, dd, dd, J 4.7, 7.9 Hz), 3.16 (3H, s), 3.94-3.99 (2H, m), 4.08 (1H, dd J 6.1, 9.6 Hz), 4.17 (1H, dd J 4.8, 9.5 Hz), 4.25 (1H, dd J 1.3, 6.3 Hz), 4.32 (1H, dd J 4.6, 9.0 Hz), 5.00 (1H, t J 4.4 Hz), 5.40 (1H, m), 5.48 (1H, m).

ESIMS: m/z 717.4 [M+Na]$^+$.

HRESIMS: calcd for C$_{34}$H$_{70}$O$_8$Si$_2$SNa: 717.4222; observed: 717.4224.

Step g: Synthesis of (2R,3R,4S,5R,6S)-5,6-di(tertiary butyldimethylsilyloxy)-3,4-O-isopropylidene-2-(methanesulfonyloxy)octadecan-1-ol [compound (8)]

To a solution of compound (7) (68 mg, 0.10 mmol) in ethyl acetate (7 mL) was added 10% Pd carbon (50 mg), and the mixture was stirred in hydrogen at room temperature for 16 hr. The catalyst was filtered off and the residue was concentrated under reduced pressure to give compound (8) (68 mg, quantitative).

IRν$_{max}$(KBr) 3526, 2928, 2856, 1517 (w), 1471, 1465, 1361, 1255, 1219, 1175 cm$^{-1}$.

$^1$H NMR (500 MHz, CDCl$_3$): δ0.10 (6H, s), 0.12 (6H, s), 0.87-0.90 (21H, m, containing two 9H singlets at 0.88 and 0.90 ppm), 1.26 (18H, bs), 1.33 (3H, s), 1.38-1.49 (2H, m), 1.51 (3H, s), 1.73-1.77 (2H, m), 3.03 (1H, dd, J 3.0, 9.4 Hz, OH), 3.16 (3H, s), 3.65 (1H, m), 3.94 (1H, m), 4.00-4.07 (2H, m), 4.22 (1H, m), 4.30 (1H, d, J 6.4 Hz), 4.90 (1H, m).

ESIMS: m/z 719.4 [M+Na]$^+$.

HRESIMS: calcd for C$_{34}$H$_{72}$O$_8$Si$_2$SNa: 719.4379; observed: 719.4380.

Step h: Synthesis of (2S,3S,4S,5R,6S)-2-azido-5,6-di(tertiary butyldimethylsilyloxy)-3,4-O-isopropylidene-octadecane [compound (9)]

A solution of compound (8) (20 mg, 0.03 mmol) and NaN$_3$ (20 mg, 0.31 mmol) in DMF (2 mL) was stirred with heating at 100° C. for 14 hr. The mixture was directly concentrated under reduced pressure, diluted with ethyl acetate, washed with water and dried over magnesium sulfate. The residue was filtered, concentrated under reduced pressure, and purified by silica gel column chromatography.

Elution thereof with hexane-ethyl acetate (9:1) gave compound (9) (14 mg, 76%).

IR$v_{max}$(KBr) 3470, 2927, 2856, 2100, 1518 cm$^{-1}$.

$^1$H NMR (500 MHz, CDCl$_3$): δ0.09 (3H, s), 0.11 (6H, s), 0.14 (3H, s), 0.87-0.92 (21H, m, containing two 9H singlets at 0.90 and 0.92 ppm), 1.26 (18H, bs), 1.32 (3H, s), 1.41 (2H, m), 1.47 (3H, s), 1.52-1.65 (2H, m), 2.03 (1H, t, J 6.1 Hz, OH), 3.66 (3H, m), 3.71 (1H, quintet, J 3.4 Hz), 3.92 (1H, m), 3.98-4.01 (2H, m), 4.08-4.12 (2H, m).

ESIMS: m/z 666.5 [M+Na]$^+$.

HRESIMS: calcd for C$_{33}$H$_{69}$N$_3$O$_5$Si$_2$Na: 666.4668; observed: 666.4667.

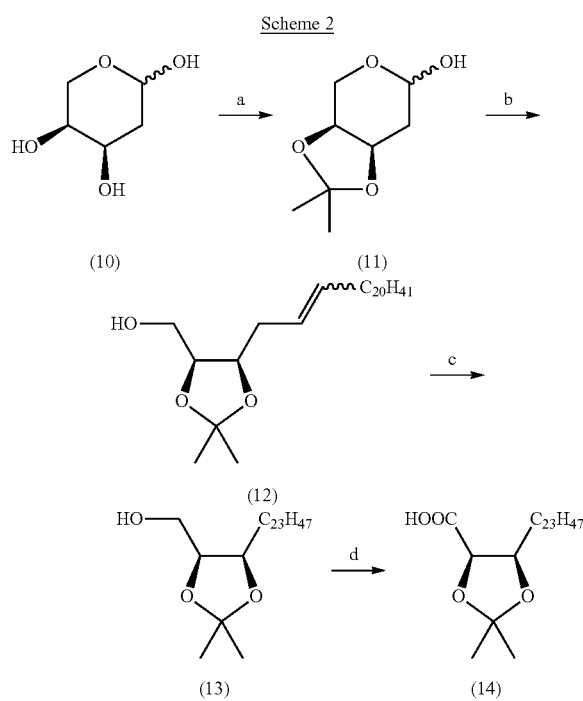

Scheme 2

Step a: Synthesis of 2-deoxy-3,4-O-isopropylidene-L-ribose [compound (11)]

To a solution of compound (10) (2-deoxy-L-ribose, 5.29 g, 39.44 mmol) in DMF (40 mL) were added 2,2-dimethoxypropane (6.16 g, 59.2 mmol) and Amberlyst 15 ion exchange resin (395 mg), and the mixture was stirred at room temperature for 18 hr. The resin was removed and the residue was concentrated under reduced pressure and purified by silica gel column chromatography. Elution thereof with hexane-ethyl acetate (3:2, further 2:3) gave compound (11) (3.41 g, 50%) as a 4:1 mixture at the anomer position. Physical Constant of Major Anomer:

IR$v_{max}$(KBr) 3534 cm$^{-1}$.

$^1$H NMR (500 MHz, CDCl$_3$): δ1.35 (3H, s), 1.51 (3H, s), 1.79 (1H, m), 2.25 (1H, ddd, J 4.1, 4.4, 14.8 Hz), 2.69 (1H, d, J 3.9 Hz, OH), 3.70 (1H, dd, J 3,4, 12.7 Hz), 3.95 (1H, dd, J 3.4, 12.7 Hz), 4.17 (1H, m), 4.48 (1H, m), 5.27 (1H, m, changed to dd, J 4.3, 7.0 Hz, on addition of D$_2$O).

EIMS: m/z 159.0 [M-Me]$^{-+}$.

HREIMS: calcd for C$_7$H$_{11}$O$_4$: 159.0657; observed: 159.0663.

Step b: Synthesis of (2S,3R)-2,3-O-isopropylidene-5-hexacosen-1-ol [compound (12)]

To a solution of henicosyltriphenylphosphonium bromide; C$_{21}$H$_{43}$P(Ph)$_3$Br (5.62 g, 8.81 mmol) in THF (19 mL) was added LiN(TMS)$_2$ (THF 1 M solution, 20.4 mL), and the mixture was stirred at 0° C. for 1 hr under an argon stream. To this red solution was added a solution of compound (11) (1.03 g, 5.91 mmol) in THF (11 mL) at 0° C., and the mixture was stirred at room temperature for 2 hr, neutralized with saturated aqueous ammonium chloride solution, and diluted with CHCl$_3$. The mixture was washed with water and 1% hydrogen peroxide, further washed with water, and dried over magnesium sulfate. The mixture was filtered, concentrated under reduced pressure, and purified by silica gel column chromatography. Elution thereof with hexane-ethyl acetate (19:1, further 9:1, finally 4:1) gave compound (12) (1.35 g, 50%) as a mixture at the anomer position.

IR$v_{max}$(KBr) 3536, 2918, 2850, 1468 cm$^{-1}$.

$^1$H NMR (500 MHz, CDCl$_3$): δ0.88 (3H, t, J 7.0 Hz), 1.25 (36H, m), 1.38 (3H, s), 1.49 (3H, s), 1.84 (1H, dd, J 5.4, 6.6 Hz), 2.04 (1H, m), 2.28 (1H, m), 2.38 (1H, m), 3.62-3.68 (2H, m), 4.15-4.23 (2H, m), 5.38 (1H, m), 5.52 (1H, m).

ESIMS: m/z 475.41 [M+Na]$^+$.

HRESIMS: calcd for C$_{29}$H$_{56}$O$_3$Na: 475.4127; observed: 475.4127.

Step c: Synthesis of (2S,3R)-2,3-O-(isopropylidene)hexacosan-1-ol [compound (13)]

Compound (12) (270 mg, 0.596 mmol) was reduced in the same manner as in the synthesis of compound (8) from compound (7), and treated by column chromatography to give compound (13) (246 mg, 91%). In the column chromatography, elution was performed with hexane-ethyl acetate (19:1, further 4:1).

IR$v_{max}$(KBr) 3458, 2924, 2848, 1468 cm$^{-1}$.

$^1$H NMR (500 MHz, CDCl$_3$): δ0.88 (3H, t, J 7.0 Hz), 1.23-1.61 (50H, m, containing two 3H singlets at 1.37 and 1.48 ppm), 1.82 (1H, dd, J 4.9, 7.3 Hz, OH), 3.59-3.63 (2H, m), 4.13-4.17 (2H, m).

ESIMS: m/z 477.4 [M+Na]$^+$. HRESIMS: calcd for C$_{29}$H$_{58}$O$_3$Na: 477.4284; observed: 477.4298.

Step d: Synthesis of (2R,3R)-2,3-O-(isopropylidene)hexacosanoic acid [compound (14)]

A solution of compound (13) (50 mg, 0.11 mmol), NaIO$_4$ (236 mg, 1.10 mmol) and RuCl$_3$.n-H$_2$O (3 mg) in CCl$_4$—CH$_3$CN—H$_2$O (2:2:3, 7 mL) was stirred at room temperature for 3 hr, and diluted with CHCl$_3$, washed with water and dried over magnesium sulfate. The residue was filtered, concentrated under reduced pressure, and purified by silica gel column chromatography. Elution thereof with hexane-ethyl acetate (6:1, further 1:2) gave compound (14) (41 mg, 80%).

IR$v_{max}$(KBr) 3290-2560, 1728, 1469 cm$^{-1}$.

$^1$H NMR (500 MHz, CDCl$_3$): δ0.88 (3H, t, J 7.0 Hz), 1.23-1.71 (50H, m, containing two 3H singlets at 1.40 and 1.61 ppm), 4.38 (1H, m), 4.55 (1H, d, J 7.3 Hz). ESIMS: m/z 467.4 [M–H]$^-$.

HRESIMS: calcd for C$_{29}$H$_{55}$O$_4$: 467.4100; observed: 467.4107.

Scheme 3

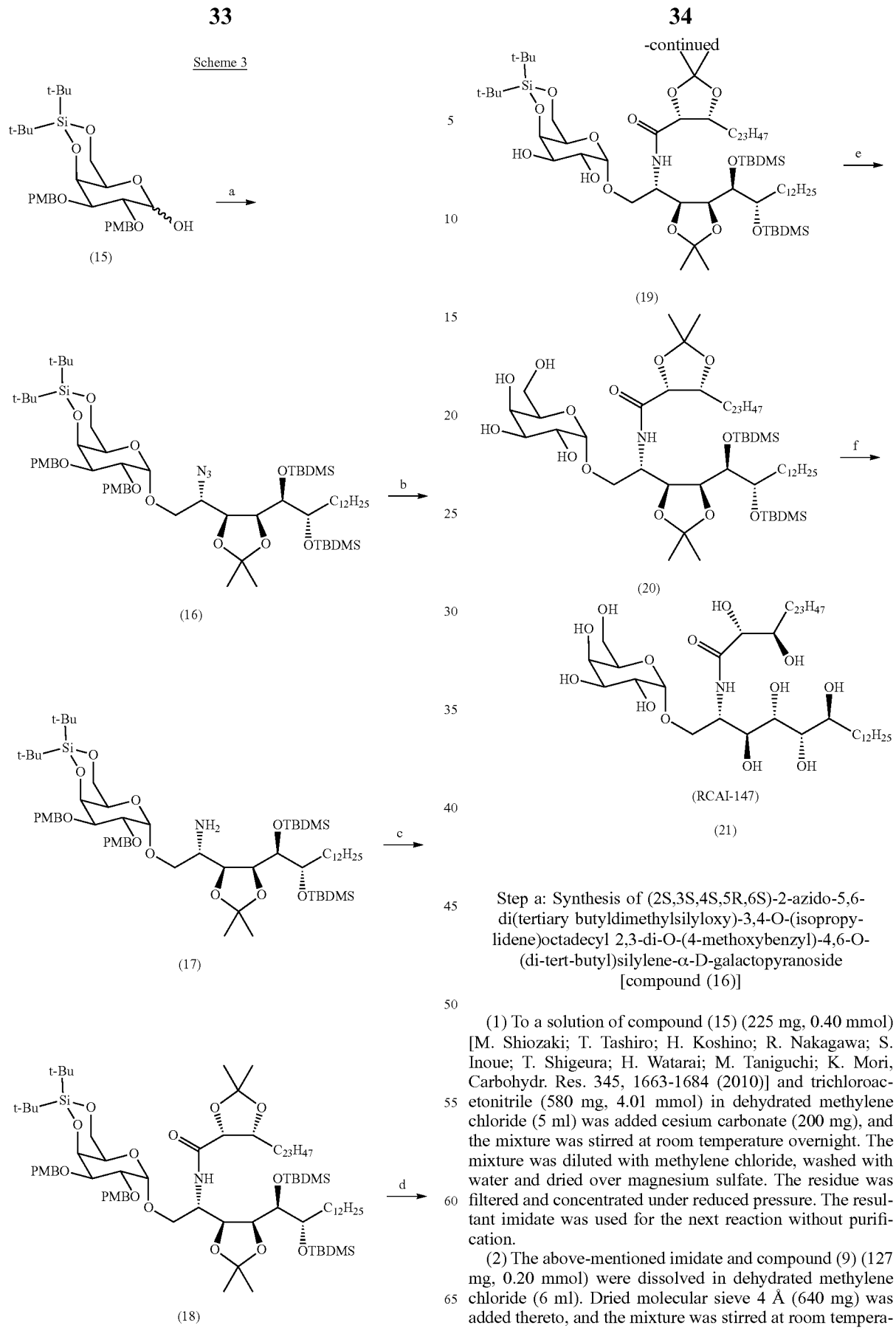

Step a: Synthesis of (2S,3S,4S,5R,6S)-2-azido-5,6-di(tertiary butyldimethylsilyloxy)-3,4-O-(isopropylidene)octadecyl 2,3-di-O-(4-methoxybenzyl)-4,6-O-(di-tert-butyl)silylene-α-D-galactopyranoside [compound (16)]

(1) To a solution of compound (15) (225 mg, 0.40 mmol) [M. Shiozaki; T. Tashiro; H. Koshino; R. Nakagawa; S. Inoue; T. Shigeura; H. Watarai; M. Taniguchi; K. Mori, Carbohydr. Res. 345, 1663-1684 (2010)] and trichloroacetonitrile (580 mg, 4.01 mmol) in dehydrated methylene chloride (5 ml) was added cesium carbonate (200 mg), and the mixture was stirred at room temperature overnight. The mixture was diluted with methylene chloride, washed with water and dried over magnesium sulfate. The residue was filtered and concentrated under reduced pressure. The resultant imidate was used for the next reaction without purification.

(2) The above-mentioned imidate and compound (9) (127 mg, 0.20 mmol) were dissolved in dehydrated methylene chloride (6 ml). Dried molecular sieve 4 Å (640 mg) was added thereto, and the mixture was stirred at room temperature for 30 min. Silvertrifluoromethanesulfonate (AgOTf, 60 mg) was added, and the mixture was stirred at 0° C. for 60 min and at room temperature for 1.5 hr. The reaction product was collected by filtration and washed with methylene chloride. The obtained solution was washed with saturated aqueous sodium hydrogen carbonate and dried over magnesium sulfate. The residue was filtered, concentrated under reduced pressure, and purified by silica gel column chromatography. Elution thereof with hexane-ethyl acetate (19:1, further 9:1) gave compound (16) (184 mg, 78%).

IR$\nu_{max}$(KBr) 2928, 2857, 2099, 1513 cm$^{-1}$.

$^1$H NMR (500 MHz, CDCl$_3$): δ0.08 (6H, s), 0.09 (3H, s), 0.13 (3H, s), 0.86-0.89 (12H, m, containing 9H singlet at 0.88 ppm), 0.91 (9H, s), 0.99 (9H, s), 1.05 (9H, s), 1.25 (18H, bs), 1.29 (3H, s), 1.38-1.44 (5H, m, containing 3H singlet at 1.43 ppm), 1.54-1.59 (2H, m), 3.61 (1H, s), 3.65 (1H, m), 3.68-3.70 (2H, m), 3.78-3.81 (7H, m, containing 6H singlet at 3.80 ppm), 3.94-3.98 (2H, m), 4.04-4.06 (2H, m), 4.09-4.13 (2H, m), 4.18 (1H, dd, J 2.0, 12.5 Hz), 4.43 (1H, d, J 3.7 Hz, galactose C$_4$—H), 4.61, 4.74 (2H, AB-q, J 11.6 Hz), 4.63, 4.66 (2H, AB-q, J 11.7 Hz), 4.75 (1H, d, J 3.4 Hz, anomeric H), 6.83-6.86 (4H, m), 7.30-7.33 (4H, m).

ESIMS: m/z 1208.7 [M+Na]$^+$.

HRESIMS: calcd for C$_{63}$H$_{111}$N$_3$O$_{12}$Si$_3$Na: 1208.7368; observed: 1208.7362.

Step b: Synthesis of (2S,3S,4S,5R,6S)-2-amino-5,6-di(tertiary butyldimethylsilyloxy)-3,4-O-(isopropylidene)octadecyl 2,3-di-O-(4-methoxybenzyl)-4,6-O-(ditertiary butyl)silylene-α-D-galactopyranoside [compound (17)]

To a solution of compound (16) (180 mg, 0.152 mmol) in THF (3 mL) was added trimethylphosphine (1M THF solution, 0.8 mL). The mixture was stirred at room temperature for 2 hr, and sodium hydroxide (1M aqueous solution, 2.9 mL) was added. The mixture was stirred at room temperature for 2 hr and diluted with chloroform (CHCl$_3$). The mixture was washed with water, filtered, concentrated under reduced pressure, and purified by silica gel column chromatography. Elution thereof with hexane-ethyl acetate (9:1, further 2:1) gave compound (17) (136 mg, 77%).

IR$\nu_{max}$(KBr) 2928, 2856, 1613, 1513, 1472, 1464, 1250 cm$^{-1}$.

$^1$H NMR (500 MHz, CDCl$_3$): δ0.03 (3H, s), 0.056 (3H, s), 0.061 (3H, s), 0.10 (3H, s), 0.86-0.89 (21H, m, containing two 9H singlets at 0.88 and 0.89 ppm), 1.00 (9H, s), 1.06 (9H, s), 1.25-1.29 (21H, bs, containing 3H singlet at 1.29 ppm), 1.39-1.42 (5H, m, containing 3H singlet at 1.42 ppm), 1.54-1.57 (4H, m, containing NH$_2$), 3.08 (1H, m), 3.28 (1H, dd, J 7.8, 10.0 Hz), 3.59 (1H, s), 3.67 (1H, m), 3.77 (1H, dd, J 2.8, 9.9 Hz), 3.79 (3H, s), 3.80 (3H, s), 3.89 (1H, m), 3.94-3.98 (3H, m), 4.03 (1H, m), 4.11 (1H, dd, J 1.6, 12.4 Hz), 4.18 (1H, dd, J 2.0, 12.4 Hz), 4.48 (1H, d, J 2.5 Hz), 4.59, 4.74 (2H, AB-q, J 11.4 Hz), 4.63, 4.66 (2H, AB-q, J 11.4 Hz), 4.76 (1H, d, J 3.4 Hz), 6.83-6.87 (4H, m), 7.26-7.34 (4H, m).

ESIMS: m/z 1160.8 [M+H]$^+$.

HRESIMS: calcd for C$_{63}$H$_{114}$NO$_{12}$Si$_3$: 1160.7643; observed: 1160.7644.

Step c: Synthesis of (2S,3S,4S,5R,6S)-5,6-di(tertiary-butyldimethylsilyloxy)-2-[(2'R,3'R)-2',3'-O-(isopropylidene)hexacosanoylamino]-3,4-O-(isopropylidene)octadecyl 2,3-O-(4-methoxybenzyl)-4,6-O-(di-tertiary butyl)silylene-α-D-galactopyranoside [compound (18)]

To a solution of compound (17) (103 mg, 0.089 mmol) and compound (14) (125 mg, 0.266 mmol, 3 eq) in THF-CH$_2$Cl$_2$ (1:1, 10 mL) were added 4-dimethylaminopyridine (DMAP) (130 mg, 1.06 mmol, 12 eq) and 1-ethyl-3-(3-dimethylaminopropyl)carbodiimide hydrochloride (EDAC) (205 mg, 1.06 mmol, 12 eq), and the mixture was stirred at room temperature for 16 hr. The mixture was diluted with CH$_2$Cl$_2$, washed with water and saturated brine, and dried over magnesium sulfate. The residue was filtered, concentrated under reduced pressure, and purified by silica gel column chromatography. Elution thereof with hexane-ethyl acetate (19:1, further 6:1) gave compound (18) (129 mg, 90%).

IR$\nu_{max}$(KBr) 2925, 2855, 1684 cm$^{-1}$.

$^1$H NMR (500 MHz, CDCl$_3$): δ0.05 (3H, s), 0.06 (3H, s), 0.09 (3H, s), 0.13 (3H, s), 0.87-0.89 (24H, m, containing two 9H, singlets at 0.88 and 0.89 ppm), 0.98 (9H, s), 1.05 (9H, s), 1.22-1.36 (71H, m, containing two 3H singlets at 1.28 and 1.31 ppm), 1.42-1.62 (7H, m, containing 3H singlet at 1.44 ppm), 3.51 (1H, m), 3.61 (1H, s), 3.72-3.78 (2H, m), 3.78-3.82 (7H, m), 3.86 (1H, m), 3.93 (1H, dd, J 3.4, 10.0 Hz), 4.06-4.11 (2H, m), 4.12-4.16 (2H, m), 4.20 (1H, m), 4.30 (1H, m), 4.38 (1H, d, J 7.3 Hz), 4.44 (1H, d, J 2.9 Hz), 4.58, 4.70 (2H, AB-q, J 11.4 Hz), 4.67 (1H, d, J 3.9 Hz, anomeric H), 6.79-6.87 (5H, m, containing NH), 7.26-7.34 (4H, m).

ESIMS: m/z 1633.15 [M+Na]$^+$.

HRESIMS: calcd for C$_{92}$H$_{167}$NO$_{15}$Si$_3$Na: 1633.1541; observed: 1633.1559.

Step d: Synthesis of (2S,3S,4S,5R,6S)-5,6-di(tertiary butyldimethylsilyloxy)-2-[(2'R,3'R)-2',3'-O-(isopropylidene)hexacosanoylamino]-3,4-(O-isopropylidene)octadecyl 4,6-O-(di-tertiary butyl)silylene-α-D-galactopyranoside [compound (19)]

To a solution of compound (18) (124 mg, 0.077 mmol) in CH$_2$Cl$_2$—H$_2$O (10:1, 19.8 mL) was added 2,3-dichloro-5,6-dicyano-1,4-benzoquinone (DDQ, 124 mg, 0.546 mmol), and the mixture was stirred for 2 hr and diluted with CH$_2$Cl$_2$. The mixture was washed with saturated aqueous sodium hydrogen carbonate and dried over magnesium sulfate. The residue was filtered, concentrated under reduced pressure, and purified by silica gel column chromatography. Elution thereof with hexane-ethyl acetate (6:1, further 3:1) gave compound (19) (99 mg, 94%).

IR$\nu_{max}$(KBr) 3405 (br), 2926, 2855, 1680, 1518, 1470 cm$^{-1}$.

$^1$H NMR (500 MHz, CDCl$_3$): δ0.05 (3H, s), 0.07 (3H, s), 0.12 (3H, s), 0.13 (3H, s), 0.88 (6H, m), 0.89 (9H, s), 0.90 (9H, s), 1.01 (9H, s), 1.06 (9H, s), 1.25 (64H, bs), 1.31 (3H, s), 1.37 (3H, s), 1.57 (3H, s), 2.52 (1H, d, J 9.5 Hz, OH), 3.39 (1H, t, J 9.8 Hz), 3.59 (1H, m), 3.62-3.73 (4H, m), 3.87 (1H, m), 4.06-4.18 (4H, m), 4.22-4.26 (2H, m), 4.34 (1H, m), 4.41 (1H, m), 4.46 (1H, d, J 7.8 Hz), 4.86 (1H, d, J 3.9 Hz, anomeric H), 6.94 (1H, d, J 8.8 Hz, NH).

ESIMS: m/z 1393.05 [M+Na]$^+$.

HRESIMS: calcd for C$_{76}$H$_{151}$NO$_{13}$Si$_3$Na: 1393.0385; observed: 1393.0405.

Step e: Synthesis of (2S,3S,4S,5R,6S)-5,6-di(tertiary butyldimethylsilyloxy)-2-[(2'R,3'R)-2',3'-O-(isopropylidene) hexacosanoylamino]-3,4-O-(isopropylidene)octadecyl α-D-galactopyranoside [compound (20)]

To a solution of compound (19) (96 mg, 0.070 mmol) and pyridine (60 mg, 0.76 mmol) in THF (7.5 mL) was added hydrofluoric acid-pyridine (HF: up to 70%; pyridine: up to 30%, 45 mg) under an argon stream at room temperature.

After 50 min, the reaction mixture was diluted with CHCl₃, washed with aqueous sodium bicarbonate, and dried over magnesium sulfate. The residue was filtered, concentrated under reduced pressure, and purified by silica gel column chromatography. Elution thereof with hexane-ethyl acetate (2:3, further 1:3) gave compound (20) (67 mg, 78%).

IR$v_{max}$(KBr) 3418 (br), 2925, 2854, 1676, 1516, 1461, 1381 cm$^{-1}$.

$^1$H NMR (500 MHz, CDCl₃): δ0.08 (3H, s), 0.10 (3H, s), 0.12 (3H, s), 0.15 (3H, s), 0.88 (6H, t, J 7.0 Hz), 0.89 (9H, s), 0.91 (9H, s), 1.25 (60H, bs), 1.31 (3H, s), 1.38 (3H, s), 1.42-1.73 (14H, m, containing two 3H singlets at 1.43 and 1.58 ppm), 2.46 (1H, dd, J 4.2, 8.4 Hz, OH), 2.63 (1H, d, J 2.5 Hz, OH), 2.68 (1H, d, J 11.5 Hz, OH), 2.83 (1H, s, OH), 3.38 (1H, dd, J 9.3, 10.8 Hz), 3.56 (1H, m), 3.69-3.79 (3H, m), 3.85-3.98 (3H, m), 4.03-4.12 (3H, m), 4.18 (1H, m), 4.25 (1H, m), 4.34 (1H, m), 4.45 (1H, d, J 7.6 Hz), 4.88 (1H, d, J 3.7 Hz, anomeric H), 7.03 (1H, d, J 9.3 Hz, NH).

ESIMS: m/z 1252.93 [M+Na]$^+$.

HRESIMS: calcd for C$_{68}$H$_{135}$NO$_{13}$Si$_2$Na: 1252.9370; observed: 1252.9390.

Step f: Synthesis of (2S,3S,4S,5S,6S)-2-[(2'R,3'R)-2',3'-(dihydroxy)hexacosanoylamino]-3,4,5,6-(tetra-hydroxy)octadecyl α-D-galactopyranoside [compound (21); RCAI-147]

To a solution of compound (20) (56 mg, 0.070 mmol) in CH₂Cl₂—CH₃CN (3:2, 28 mL) were added H₂O (423 mg) and 46% HF water (423 mg), and the mixture was stirred at room temperature for 16 hr. Since the object product was precipitated, it was directly collected by filtration, and washed well with saturated aqueous sodium hydrogen carbonate and water. Finally, the mixture was washed with a small amount of CHCl₃—CH₃CN (1:1) and dried under reduced pressure. The residue was purified by silica gel column chromatography. Elution thereof with CHCl₃-MeOH (9:1, further 7:1, finally 5:1) gave compound (21) (20 mg, 48%). Compound (21) was named RCAI-147.

[α]$_D^{28}$+49.6 (c 0.52, pyridine).

IR$v_{max}$(KBr) 3361 (br), 2920, 2851, 1646, 1542, 1468 cm$^{-1}$.

$^1$H NMR (500 MHz, pyridine-d₅, one drop of 1% TMS in CDCl₃): δ0.87 (6H, t, J 7.0 Hz), 1.22-1.33 (60H, m), 1.53-1.62 (2H, m), 1.80-2.02 (5H, m), 2.26 (1H, m), 4.31-4.40 (4H, m), 4.43-4.48 (3H, m), 4.51-4.55 (2H, m), 4.63 (1H, dd, J 3.7, 9.8 Hz), 4.70 (1H, d, J 5.1 Hz), 4.73 (1H, dd, J 6.2, 10.8 Hz), 4.83 (1H, dd, J 3.1, 8.5 Hz), 4.99 (1H, m), 5.40 (1H, m), 5.57 (1H, d, J 3.7 Hz), 8.71 (1H, d, J 9.5 Hz, NH).

$^{13}$C NMR (125 MHz, pyridine-d₅): 14.26, 22.91, 26.42, 26.45, 29.58, 29.89, 29.95, 29.98, 30.02, 30.13, 30.16, 30.18, 30.32, 32.09, 32.69, 35.16, 50.89, 62.58, 67.89, 70.24, 70.91, 71.31, 71,59, 72.72, 72.73, 72.97, 73.49, 73.80, 76.02, 101,08, 173.98.

ESIMS: m/z 944.70 [M+Na]$^+$.

HRESIMS: calcd for C$_{50}$H$_{99}$NO$_{13}$Na: 944.7014; observed: 944.7007.

Example 2

Synthesis and Purification Method of RCAI-151

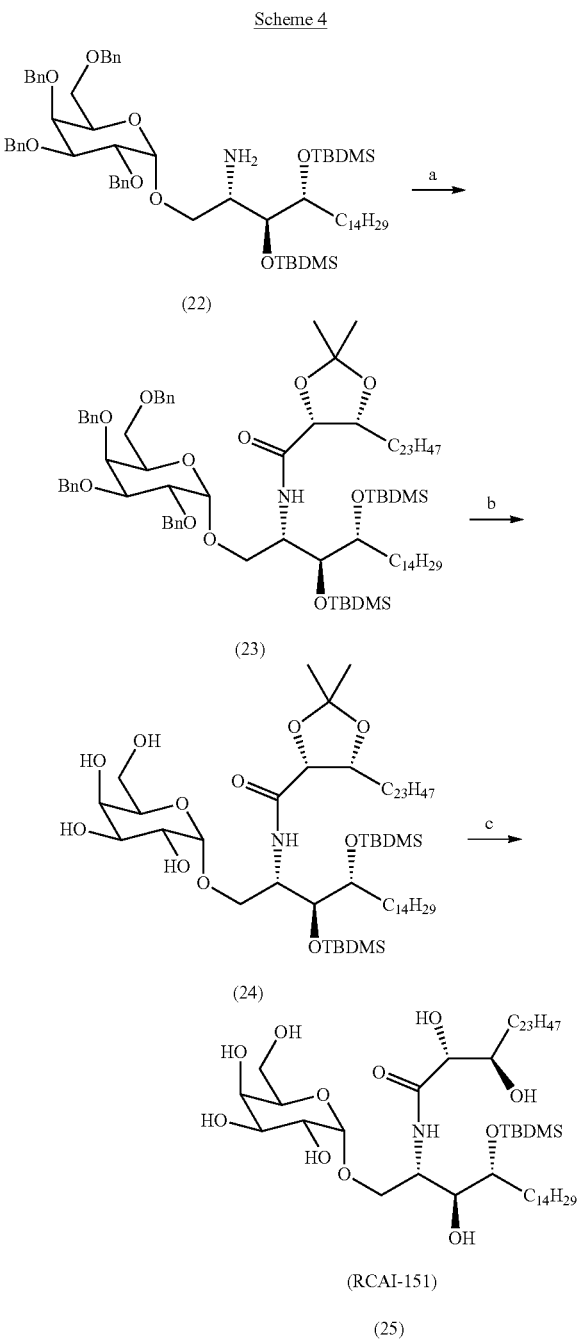

Scheme 4

Step a: Synthesis of (2S,3S,4R)-3,4-(di-tertiary butyldimethylsilyloxy)-2-[(2'R,3'R)-2',3'-O-isopropylidenehexacosanoylamino]octadecyl 2,3,4,6-tetra-O-benzyl-α-D-galactopyranoside [compound (23)]

To a solution of compound (22) (160 mg, 0.15 mmol) [Tashiro, T.; Hongo, N.; Nakagawa, R.; Seino, K.; Watarai, H.; Ishii, Y.; Taniguchi, M.; Mori, K. Bioorg. & Med. Chem.

2008, 16, 8896-8906] in THF-CH$_2$Cl$_2$ (1:1, 16 mL) were added 4-dimethylaminopyridine (DMAP) (220 mg, 1.80 mmol), compound (14) (210 mg, 0.45 mmol) and EDAC (345 mg, 1.80 mmol), and the mixture was stirred at room temperature for 15 hr. The mixture was concentrated under reduced pressure and diluted with CH$_2$Cl$_2$. The mixture was washed with water, and dried over magnesium sulfate. The residue was filtered, concentrated under reduced pressure, and purified by silica gel column chromatography. Elution thereof with hexane-ethyl acetate (19:1, further 6:1) gave compound (23) (177 mg, 78%).

IR$\nu_{max}$(KBr) 2925, 2853, 1686 cm$^{-1}$.

$^1$H NMR (500 MHz, CDCl$_3$): δ0.047 (3H, s), 0.054 (3H, s), 0.055 (3H, s), 0.11 (3H, s), 0.87-0.90 (24H, m), 1.20 (3H, s), 1.25 (62H, bs), 1.31-1.40 (4H, m), 1.44 (3H, s), 1.46-1.60 (2H, m), 1.65-1.70 (2H, m), 3.47 (1H, dd, J 5.7, 9.1 Hz), 3.54 (1H, t, J 8.4 Hz), 3.69-3.72 (2H, m), 3.81-3.85 (2H, m), 3.91-3.95 (2H, m), 3.99 (1H, d, J 1.7 Hz), 4.04 (1H, d, J 3.5, 10.1 Hz), 4.18 (1H, m), 4.27 (1H, m), 4.37, 4.48 (2H, AB-q, J 11.7 Hz), 4.40 (1H, d, J 7.6 Hz), 4.55, 4.91 (2H, AB-q, J 11.3 Hz), 4.70, 4.74 (2H, AB-q, J 11.7 Hz), 4.70-4.81 (2H, AB-q, J 11.7 Hz), 4.87 (1H, d, J 3.5 Hz), 6.80 (1H, d, J 9.5 Hz, NH), 7.24-7.36 (20H, m).

ESIMS: m/z 1541.10 [M+Na]$^+$.

HRESIMS: calcd for C$_{93}$H$_{155}$NO$_{11}$Si$_2$Na: 1541.1036; observed: 1541.0992.

Step b: Synthesis of (2S,3S,4R)-3,4-(di-tert-butyldimethylsilyloxy)-2-[(2'R,3'R)-2',3'-O-isopropylidenehexacosanoylamino]octadecyl α-D-galactopyranoside [compound (24)]

To a solution of compound (23) (160 mg, 0.105 mmol) in THF (40 mL) was added 20% Pd(OH)$_2$/C (300 mg), and the mixture was stirred at room temperature for 16 hr under a hydrogen stream. The catalyst was removed, and the residue was concentrated under reduced pressure and purified by silica gel column chromatography. Elution thereof with hexane-ethyl acetate (1:1, further 1:4) gave compound (24) (94 mg, 77%).

IR$\nu_{max}$(KBr) 3415, 2925, 2854, 1667, 1523, 1466 cm$^{-1}$.

$^1$H NMR (500 MHz, CDCl$_3$): δ0.07 (3H, s), 0.08 (3H, s), 0.12 (3H, s), 0.14 (3H, s), 0.88 (6H, t, J 7.0 Hz), 0.91 (9H, s), 0.92 (9H, s), 1.25 (62H, bs), 1.37 (3H, s), 1.45-1.67 (11H, m, containing 3H singlet at 1.53 ppm), 2.25 (1H, d, J 10.8 Hz, OH), 2.46 (1H, dd, J 4.8, 7.7 Hz, OH), 2.61 (1H, d, J 3.7 Hz, OH), 2.84 (1H, s, OH), 3.50 (1H, dd, J 8.3, 11.0 Hz), 3.67-3.87 (6H, m), 3.92 (1H, m), 4.09 (1H, s), 4.15 (1H, dd, J 3.2, 10.8 Hz), 4.34-4.40 (2H, m), 4.52 (1H, d, J 7.4 Hz), 4.90 (1H, d, J 3.6 Hz), 671 (1H, d, J 9.8 Hz, NH).

ESIMS: m/z 1180.91 [M+Na]$^+$.

HRESIMS: calcd for C$_{55}$H$_{131}$NO$_{11}$Si$_2$Na: 1180.9158; observed: 1180.9149.

Step c: Synthesis of (2S,3S,4R)-3,4-dihydroxy-2-[(2'R,3'R)-2',3'-dihydroxyhexacosanoylamino]octadecyl α-D-galactopyranoside [compound (25) (RCAI-151)]

Compound (25) (40 mg, 63%) was obtained by treating compound (24) (80 mg, 0.071 mmol) in the same manner as in the synthesis of compound (21) from compound (20). In column chromatography, elution was performed with CHCl$_3$-MeOH (9:1, further 6:1). The obtained compound (25) was named RCAI-151.

[α]$_D^{29}$+62.4 (c 1.04, pyridine).

IR$\nu_{max}$(KBr) 3364, 2918, 2850, 1646, 1636, 1541, 1469 cm$^{-1}$.

$^1$H NMR (500 MHz, pyridine-d$_5$, one drop of 1% TMS in CDCl$_3$): δ0.88 (6H, t, J 6.8 Hz), 1.20-1.34 (60H, m), 1.34-1.49 (2H, m), 1.60-1.71 (2H, m), 1.82-1.96 (3H, m), 2.00-2.08 (2H, m), 2.31 (1H, m), 4.27 (1H, m), 4.32-4.43 (4H, m), 4.47-4.57 (4H, m), 4.64-4.70 (2H, m), 4.74 (1H, m), 5.33 (1H, m), 5.61 (1H, d, J 3.7 Hz), 8.65 (1H, d, J 9.5 Hz, NH).

$^{13}$C NMR (125 MHz, pyridine-d$_5$): 14.31, 22.96, 26.48, 26.55, 29.64, 29.65, 29.94, 29.97, 30.01, 30.03, 30.05, 30.09, 30.19, 30.22, 30.30, 30.47, 32.15, 32.16, 32.64, 34.62, 50.57, 62.67, 67.99, 70.24, 71.02, 71.65, 72.37, 73.13, 73.55, 76.21, 76.55, 101,20, 173.79.

ESIMS: m/z 912.72 [M+Na]$^+$.

HRESIMS: calcd for C$_{50}$H$_{99}$NO$_{11}$Na: 912.7116; observed: 912.7134.

Example 3

Synthesis and Purification Method of RCAI-160

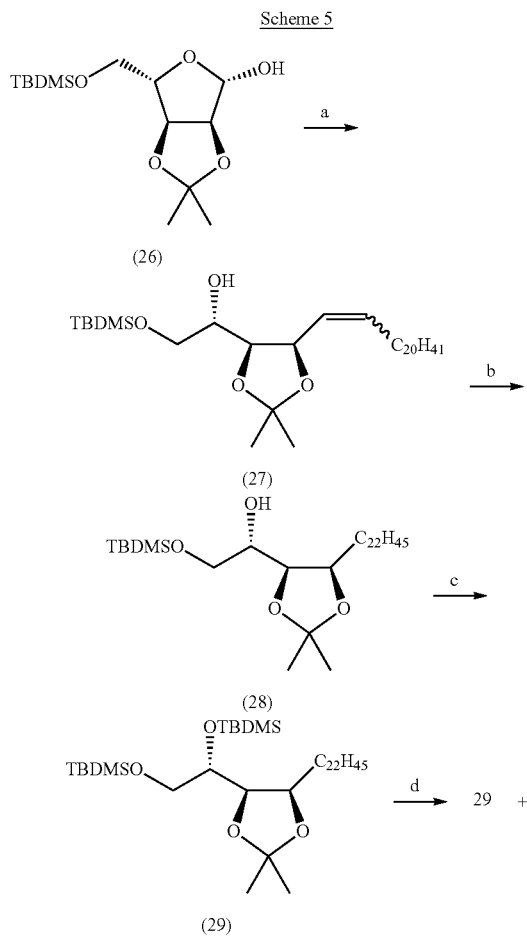

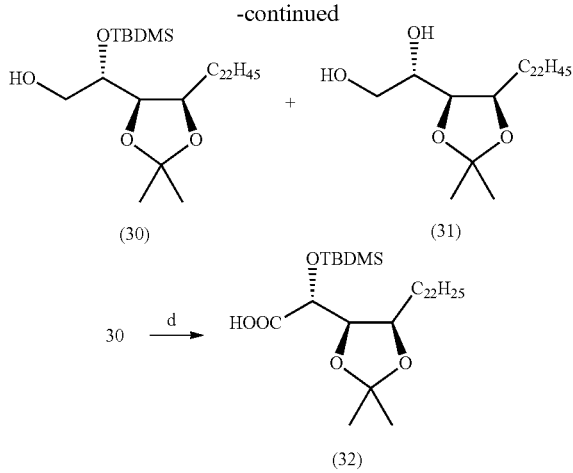

(30)  (31)  (32)

Step a: Synthesis of (2S,3S,4R,5EZ)-1-(tertiary butyldimethylsilyloxy)-3,4-O-isopropylidene-5-hexacosenyl-2-ol [compound (27)]

To a solution of heneicosyltriphenylphosphonium bromide (638 mg, 1.00 mmol) in dried THF (3 ml) was added with stirring a solution of n-BuLi (1.57 M hexane solution, 1.20 mL, 1.88 mmol) at −10° C. under an argon stream. After stirring at this temperature for 30 min, to the solution was added a solution of 5-O-tertiary butyldimethylsilyl-2,3-O-isopropylidene-L-libofuranose (compound (26), 152 mg, 0.50 mmol) in dried THF (2 mL). The solution was stirred at room temperature for 4 hr, treated with methanol under ice-cooling and diluted with ethyl acetate. The diluted solution was washed with water and saturated brine and dried over MgSO$_4$. The residue was filtered, concentrated, and purified by silica gel column chromatography. Elution thereof with hexane-ethyl acetate (39:1, further 19:1) gave compound (27) (183 mg, 63%) as a mixture of E,Z-geometric isomers.

IRv$_{max}$(KBr):3540, 2926, 2855, 1465 cm$^{-1}$.
$^1$H NMR (500 MHz, CDCl$_3$): δ0.09 (6H, s), 0.88 (3H, t, J 6.8 Hz), 0.91 (9H, s), 1.25-1.44 (41H, m, containing 3H, s, at 1.34 ppm), 1.45 (3H, s), 2.02-2.20 (2H, m), 2.45 (1H, d, J 4.6 Hz, OH), 3.66-3.71 (2H, m), 3.81 (1H, m), 3.83-4.03 (1H, m), 4.64 (0.6H, m), 5.00 (0.4H, dd, J 7.1, 8.8 Hz), 5.51-5.85 (2H, m).
ESMS: m/z 605.49 [M+Na]$^+$.
HRESMS: Calcd for C$_{35}$H$_{70}$O$_4$SiNa: 605.4941; observed, 605.4952.

Step b: Synthesis of (2S,3S,4R)-1-(tertiary butyldimethylsilyloxy)-3,4-O-isopropylidene-5-hexacosan-2-ol [compound (28)]

Using a solution of compound (27) (3.45 g, 5.92 mmol), which is an E,Z isomer mixture, in ethyl acetate (120 ml), the double bond was reduced with 20% Pd(OH)$_2$/C (1.3 g) under a hydrogen stream at room temperature for 1 hr. The catalyst was filtered off and the residue was concentrated to quantitatively give compound (28) (3.45 g).

IRv$_{max}$(KBr):3539 (br), 2923, 2853, 1464 cm$^{-1}$.
$^1$H NMR (500 MHz, CDCl$_3$) δ0.09 (6H, s), 0.88 (3H, t, J=6.8 Hz), 0.91 (9H, s), 1.26 (38H, bs), 1.32 (3H, s), 1.40 (3H, s), 1.50-1.80 (4H, m), 2.57 (1H, d, J 3.9 Hz), 3.64-3.69 (2H, m), 3.82 (1H, m), 3.91 (1H, dd, J 5.7, 8.8 Hz), 4.17 (1H, m).
ESMS: m/z 607.51 [M+Na]$^+$.
HRESMS: calcd. for C$_{35}$H$_{72}$O$_4$SiNa: 607.5098; observed, 607.5100.

Step c: Synthesis of (2S,3R,4R)-1,2-di(tertiary butyldimethylsilyloxy)-3,4-O-isopropylidenehexacosane [compound (29)]

To a solution (150 ml) of compound (28) (3.45 g, 5.90 mmol) in methylene chloride were added 2,6-lutidine (3.17 g, 29.6 mmol) and tertiary butyldimethylsilyl trifluoromethanesulfonate (4.69 g, 17.8 mmol), and the mixture was stirred at room temperature for 1 hr. The mixture was diluted with methylene chloride, washed with saturated aqueous sodium hydrogen carbonate and brine, and dried over MgSO$_4$. The residue was filtered, concentrated, and purified by silica gel column chromatography. Elution thereof with hexane-ethyl acetate (39:1) gave compound (29) (3.71 g, 90%).

IRv$_{max}$(KBr):2925, 2855, 1464, 1254 cm$^{-1}$.
$^1$H NMR (500 MHz, CDCl$_3$) δ0.06 (6H, s), 0.09 (3H, s), 0.12 (3H, s), 0.87 (9H, s), 0.88 (3H, t, J=7.0 Hz), 0.91 (9H, s), 1.26 (40H, bs), 1.31 (3H, s), 1.40 (3H, s), 1.52-1.54 (2H, m), 3.72 (1H, m), 3.76-3.81 (2H, m), 4.03-4.10 (2H, m).
ESMS: m/z 641.58, 659.58, 721.60 [M+Na]$^+$.
HRESMS: calcd for C$_{41}$H$_{86}$O$_4$Si$_2$Na: 721.5962; observed: 721.5974.

Step d: Synthesis of (2S,3R,4R)-2-tertiary butyldimethylsilyloxy-3,4-O-isopropylidenehexacosan-1-ol [compound (30)] and (2S,3S,4R)-1,2-dihydroxy-3,4-O-isopropylidenehexacosan [compound (31)]

To a solution of compound (29) (100 mg, 0.14 mmol) in pyridine (0.9 ml) and THF (1 ml) was added HF-pyridine (0.2 ml; HF: up to 70%, pyridine: up to 30%), and the mixture was stirred at room temperature for 16 hr. The mixture was diluted with ethyl acetate, washed with saturated aqueous sodium hydrogen carbonate and brine, and dried over MgSO$_4$. The residue was filtered, concentrated, and purified by silica gel column chromatography. Elution thereof with hexane-ethyl acetate (19:1, further 4:1, finally 1:1) recovered starting material (32 mg, 32%), compound (30) (39 mg, 46%) and compound (31) (10 mg, 15%).
Compound (30)
IRv$_{max}$(KBr):3496 (br), 2925, 3854 cm$^{-1}$.
$^1$H NMR (500 MHz, CDCl$_3$) δ0.11 (3H, s), 0.13 (3H, s), 0.87-0.89 (12H, m), 1.25-1.34 (40H, m), 1.35 (3H, s), 1.43 (3H, s), 1.50-1.58 (2H, m), 2.27 (1H, dd, J=3.7, 9.1 Hz, OH), 3.68-3.77 (2H, m), 3.83 (1H, m), 4.07 (1H, dd, J=5.7, 8.2 Hz), 4.13 (1H, m).
TOFESMS: m/z 607.51 [M+Na]$^+$.
HRESMS: calcd. for C$_{35}$H$_{72}$O$_4$SiNa: 607.5098; observed, 607.5090.
Compound (31)
IRv$_{max}$(KBr):3355, 2917, 2850, 1472 cm$^{-1}$.
$^1$H NMR (500 MHz, CDCl$_3$) δ0.88 (3H, t, J=7.0 Hz), 1.24-1.75 (48H, m, containing two 3H singlets at 1.34 and 1.42 ppm), 1.91 (1H, m, OH), 2.18 (1H, d, J=5.6 Hz, OH), 3.72-3.76 (2H, m), 3.82 (1H, m), 3.96 (1H, m), 4.20 (1H, m).
TOFESMS: m/z 493.42 [M+Na]$^+$.
HRESMS: calcd. for C$_{29}$H$_{58}$O$_4$Na: 493.4233; observed, 493.4227.

43

Step e: Synthesis of (2R,3R,4R)-2-tertiary butyldimethylsilyloxy-3,4-O-isopropylidenehexacosanoic acid [compound (32)]

To a solution of compound (30) (66 mg, 0.113 mmol) in $CCl_4$—$CH_3CN$—$H_2O$ (2:2:3, 7 mL) were added $NaIO_4$ (242 mg, 1.13 mmol) and $RuCl_3 \cdot nH_2O$ (3 mg), and the mixture was stirred at room temperature for 3 hr, and diluted with $CHCl_3$. This solution was washed with water and dried over $MgSO_4$. The residue was filtered, concentrated and purified by silica gel column chromatography. Elution thereof with hexane-ethyl acetate (19:1, further 4:1) gave compound (32) (52 mg, 77%).

$IRv_{max}$(KBr):2924, 2853, 1725, 1465 $cm^{-1}$.

$^1$H NMR (500 MHz, $CDCl_3$): δ0.11 (3H, s), 0.14 (3H, s), 0.88 (3H, t, J 6.8 Hz), 0.92 (9H, s), 1.25 (40H, bs), 1.34 (3H, s), 1.45 (3H, s), 1.54-1.66 (2H, m), 4.19-4.20 (2H, m), 4.30 (1H, d, J 6.1 Hz).

ESMS: m/z 621.49 $[M+Na]^+$.

HRESMS: calcd for $C_{35}H_{70}O_5SiNa$: 621.4890; observed: 621.4877.

Scheme 6

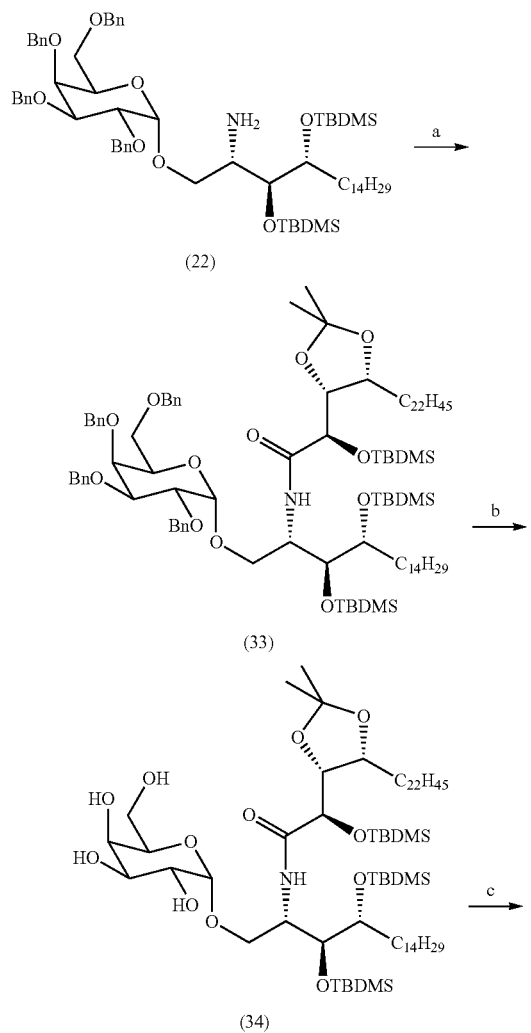

44

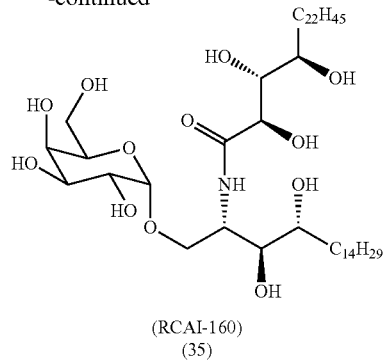

(RCAI-160)
(35)

Step a: (2S,3S,4R)-2-[(2'R,3'R,4'R)-2'-tertiary butyldimethylsilyloxy-3',4'-O-isopropylidenehexacosanoyl]amino-3,4-di-(tertiary butyldimethylsilyloxy) octadecyl-2,3,4,6-tetra-O-benzyl-α-D-galactopyranoside [synthesis of compound (33)]

To a solution of amine compound (22) (200 mg, 0.19 mmol), 4-dimethylaminopyridine (320 mg, 2.62 mmol) and carboxylic acid compound (32) (336 mg, 0.56 mmol) in THF-$CH_2Cl_2$ (1:1, 20 ml) was added 1-ethyl-3-(3-dimethylaminopropyl)carbodiimide hydrochloride (EDAC, 503 mg, 2.62 mmol), and the mixture was stirred at room temperature for 32 hr. The solvent was evaporated under reduced pressure. The residue was diluted with $CH_2Cl_2$, and the solution was washed with water and dried over $MgSO_4$. The residue was filtered, concentrated and purified by silica gel column chromatography. Elution thereof with hexane-ethyl acetate (19:1, further 9:1) gave compound (33) (116 mg, 38%).

$IRv_{max}$(KBr):2925, 2854, 1685 $cm^{-1}$.

$^1$H NMR (500 MHz, $CDCl_3$): δ0.05 (3H, s), 0.06 (3H, s), 0.068 (3H, s), 0.072 (3H, s), 0.10 (6H, s), 0.87-0.90 (33H, m), 1.25 (67H, bs), 1.40 (3H, s), 1.44-1.54 (4H, m), 3.48 (1H, m), 3.58 (1H, t, J 8.5 Hz), 3.71-3.77 (3H, m), 3.90 (1H, dd, J 2.8, 10.3 Hz), 3.98-4.07 (5H, m), 4.22-4.27 (2H, m), 4.33 (1H, m), 4.37, 4.88 (2H, AB-q, J 11.7 Hz), 4.49, 4.53 (2H, AB-q, J 11.5 Hz), 4.69, 4.74 (2H, AB-q, J 12.0 Hz), 4.69, 4.75 (2H, AB-q, J 12.0 Hz), 4.87 (1H, d, J 3.4 Hz, anomeric H), 6.62 (1H, d, J 8.3 Hz, NH), 7.24-7.35 (20H, m).

TOFESMS: m/z 1650.21 $[M+H]^+$.

HRESMS: calcd for $C_{99}H_{170}NO_{12}Si_3$: 1649.2031; observed: 1649.2056.

Step b: (2S,3S,4R)-2-[(2'R,3'R,4'R)-2'-tertiary butyldimethylsilyloxy-3',4'-O-isopropylidenehexacosanoyl]amino-3,4-di-(tertiary butyldimethylsilyloxy) octadecyl-α-D-galactopyranoside [synthesis of compound (34)]

Hydrogenolysis of a solution of compound (33) (116 mg, 0.041 mmol) in tetrahydrofuran (30 mL) was performed using $Pd(OH)_2$/C (200 mg) as a catalyst for 16 hr. The mixture was filtered, concentrated, and purified by silica gel column chromatography. Elution thereof with hexane-ethyl acetate (2:1, further 1:2) gave compound (34) (68 mg, 73%).

$IRv_{max}$(KBr):3419 (br), 2925, 2854, 1684, 1465 $cm^{-1}$.

$^1$H NMR (500 MHz, $CDCl_3$): δ0.08 (3H, s), 0.09 (3H, s), 0.12-0.13 (12H, m), 0.88 (6H, t, J 7.1 Hz), 0.90 (9H, s), 0.92 (9H, s), 0.93 (9H, s), 1.25 (64H, bs), 1.31 (3H, s), 1.42 (3H, s), 1.50-1.62 (4H, m), 2.45 (1H, bs, OH), 2.61-2.80 (3H, m, OH), 3.42 (1H, t, J 10.5 Hz), 3.65 (1H, t, J 2.7 Hz), 3.68-3.75 (3H, m), 3.83-3.87 (2H, m), 3.92 (1H, m), 4.08 (1H, m), 4.12 (1H, m), 4.21 (2H, s), 4.30 (1H, m), 4.49 (1H, m), 4.88 (1H, d, J 3.4 Hz), 6.46 (1H, d, J 10.0 Hz, NH).

TOFESMS: m/z 1289.01 [M+H]$^+$. 1290.02, 1291.02.

HRESMS: calcd for $C_{71}H_{146}NO_{12}Si_3$: 1289.0153; observed: 1289.0162.

Step c: Synthesis of (2S,3S,4R)-2-[(2'R,3'R,4'R)-2', 3',4'-trihydroxyhexacosanoyl]amino-3,4-di-hydroxyoctadecyl α-D-galactopyranoside [compound (35) (RCAI-160)]

Compound (34) (46 mg, 0.04 mmol) was treated in the same manner as when compound (25) was obtained from compound (24), and purified by silica gel column chromatography. Elution thereof with CHCl$_3$-MeOH (9:1, further 6:1) gave compound (35) (16 mg, 48%). Compound (35) was named RCAI-160.

$[α]_D^{25}$ +56.2 (c 0.75, pyridine).

IR$ν_{max}$ KBr:3372 (br), 2920, 2851, 1638, 1541, 1469 cm$^{-1}$.

$^1$H NMR (500 MHz, pyridine-d$_5$, one drop of 1% TMS in CDCl$_3$): δ 0.88 (6H, t, J 6.9 Hz), 1.20-1.45 (60H, m), 1.58-1.69 (2H, m), 1.79 (1H, m), 1.85-1.97 (3H, m), 2.20-2.29 (2H, m), 4.26-4.35 (3H, m), 4.36-4.41 (2H, m), 4.43-4.52 (4H, m), 4.55 (1H, s), 4.66 (1H, dd, J 3.8, 9.9 Hz), 4.70 (1H, dd, J 5.8, 10.7 Hz), 5.05 (1H, s), 5.32 (1H, m), 5.60 (1H, d, J 3.7 Hz, anomeric H), 6.11 (1H, bs, OH), 6.16 (1H, bs, OH), 6.35 (1H, bs, OH), 6.56 (1H, bs, OH), 6.66 (1H, bs, OH), 6.67 (1H, bs, OH), 6.73 (1H, bs, OH), 7.05 (1H, bs, OH), 7.66 (1H, bs, OH), 8.70 (1H, d, J 9.0 Hz, NH).

$^{13}$C NMR (125 MHz, pyridine-d$_5$, one drop of 1% TMS in CDCl$_3$): 14.39, 23.05, 26.45, 26.58, 29.71, 29.73, 30.02, 30.04, 30.07, 30.09, 30.10, 30.11, 30.14, 30.26, 30.46, 30.51, 32.22, 32.23, 34.63, 34.81, 51.15, 62.74, 67.84, 70.34, 71.09, 71.70, 72.39, 73.06, 73.14, 74.37, 76.16, 77.77, 101,24, 174.29.

TOFESMS: m/z 928.70 [M+Na]$^+$.

HRESMS: calcd for $C_{50}H_{99}NO_{12}Na$: 928.7065; observed: 928.7056.

Experimental Example 1

Biological Activity Test of Hydroxylated Glycolipid of the Present Invention

Solutions of each of KRN7000, RCAI-147, RCAI-151, and RCAI-160 in dimethyl sulfoxide (DMSO) at a concentration of 1 mg/mL were prepared. The above-mentioned DMSO solutions were diluted 5-fold with 0.5% Tween 20 (Bio-Rad)-containing phosphate buffer (Invitrogen) and further diluted 20-fold with phosphate buffer, such that the dose became 100 μg/kg body weight when 200 μL was administered per mouse from the tail vein.

To three C57BL/6 mice per group was injected each prepared solution (200 μL) of RCAI-147, RCAI-151 and RCAI-160 into the tail vein (administration of about 2 μg per mouse). As a control substance, KRN7000 was used, and a solution (200 μL) of KRN7000 prepared in the same manner such that the dose became 100 μg/kg body weight was injected into the tail vein. The blood (80 μL) immediately before administration, and after lapse of 1, 3, 6, 12, 24, 32, 48 and 60 hr was collected from orbital plexus venosus, and plasma was prepared.

The content of each cytokine in plasma immediately before and after administration of each glycolipid was measured by Cytometric Bead Array (CBA) system (BD Biosciences) which is one of the ELISA methods.

Figure 2:
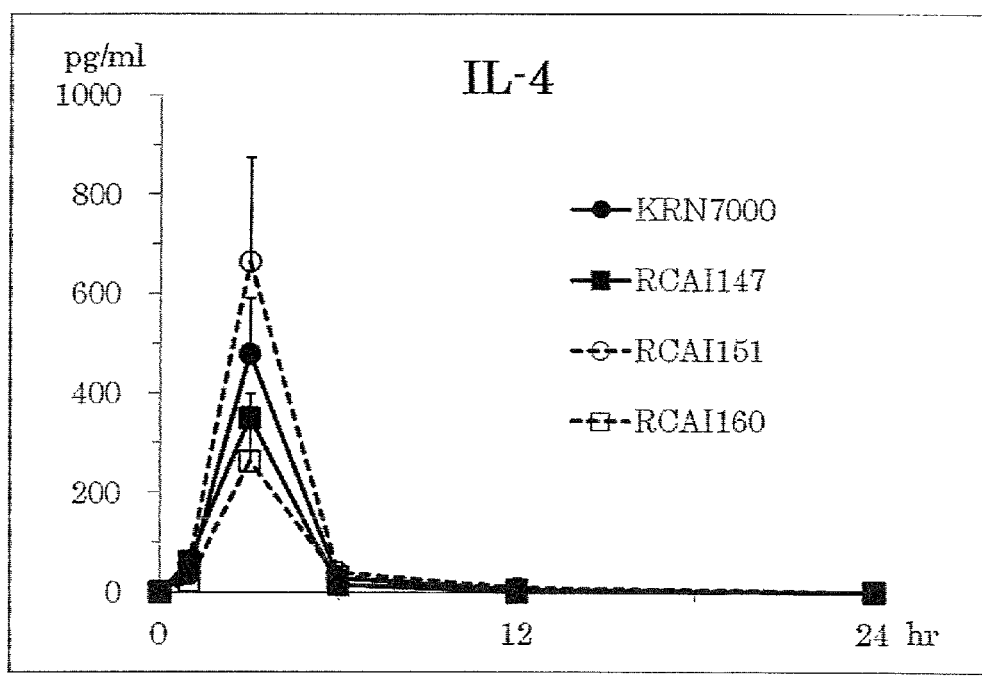
FIG. 2 is a graph showing changes in the IL-4 concentration of mouse plasma after lapse of an indicated time after intravenous administration of various glycolipids to mouse.

The measurement results (mean) and standard deviation thereof (STDEV) of the content of IFN-γ in plasma immediately before administration, and after lapse of 3, 6, 12, 24, 32, 48 and 60 hr are shown in FIG. 1. The measurement results (mean) and standard deviation thereof (STDEV) of the content of IL-4 in plasma immediately before administration, and after lapse of 1, 3, 6, 12 and 24 hr from the administration are shown in FIG. 2.

The above-mentioned results reveal that RCAI-147, RCAI-151 and RCAI-160 have a cytokine production induction activity biased to the IL-4 as compared to KRN7000. That is, it was confirmed that these glycolipids which are hydroxylated analogs of KRN7000 can induce production of cytokine biased to the Th2 type.

Experimental Example 2

Effect of Hydroxylated Glycolipid of the Present Invention on the Onset of EAE (Experimental Encephalomyelitis)

(1) Induction of EAE Onset

Pertussis toxin (5 μg/ml) was subcutaneously administered (200 μl) to C57BL/6J (female) mouse, and MOG peptide emulsion [rat MOG partial peptide (35th-55th) 6 mg/ml: CFA (complete Freund adjuvant)=1:1] (100 μl) was intraperitoneally administered twice, after which pertussis toxin alone was administered 48 hr later to induce onset of EAE.

(2) Preadministration of Dendritic Cell Pulsed with Various Glycolipids

Figure 3:
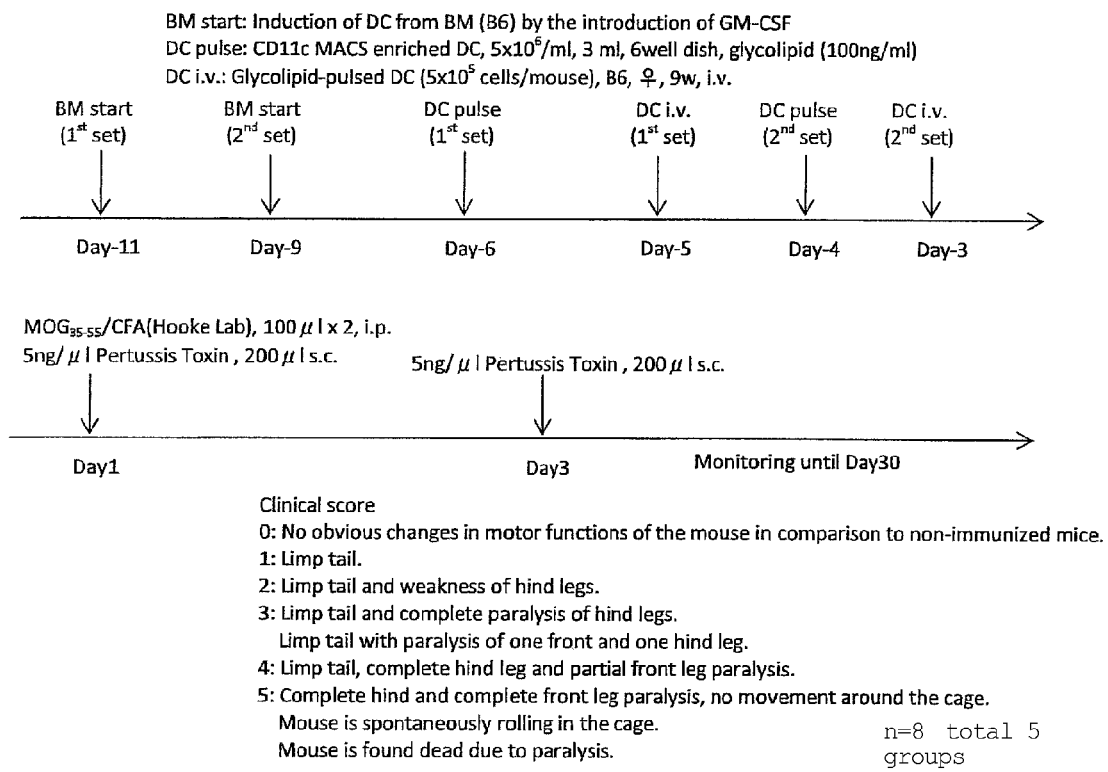
FIG. 3 is a graph showing the Scheme of an EAE evaluation system. Using the evaluation system, clinical scores of mice administered with dendritic cells pulsed with various glycolipids are measured.

Dendritic cells pulsed with various glycolipids (KRN-7000, RCAI-147, RCAI-151, RCAI-160) were intravenously administered according to the schedule shown in FIG. 3 to the mouse before induction of the onset of EAE.

(3) Evaluation of Onset Suppressive Effect

The effect of administration of dendritic cells pulsed with various glycolipids on the suppression of the onset of EAE was examined. The evaluation included observation of the onset symptoms every day from the start of the administration. The evaluation was scored according to the following criteria.

Figure 4:
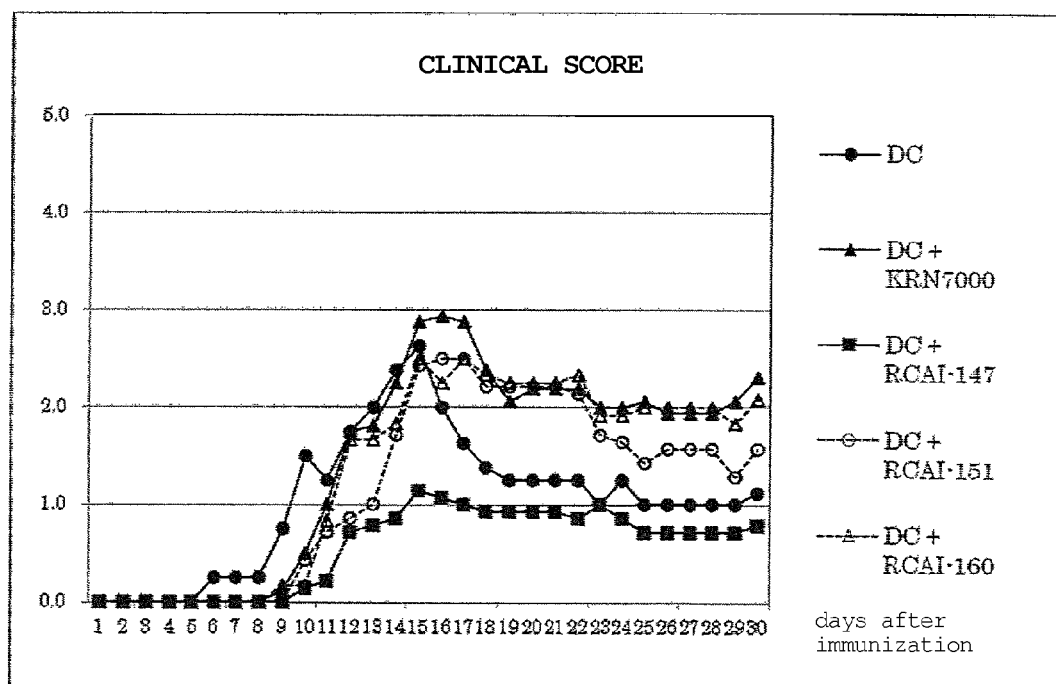
FIG. 4 is a graph showing clinical scores in the EAE evaluation system when dendritic cells pulsed with various glycolipids are administered.

0: no obvious changes in motility functions in comparison to mouse without administration of dendritic cells
1: no tension of tail
2: no tension of tail and weakness of hind legs
3: no tension of tail and complete paralysis of hind legs
   no tension of tail and paralysis of one front leg and one hind leg
4: no tension of tail and complete paralysis of hind legs and partial paralysis of front legs
5: complete paralysis of front legs and hind legs, no movement around the cage
   spontaneously rolling in the cage
   mouse is found dead due to paralysis (4) Results The results of the clinical scores from day 1 to day 30 after immunization with pertussis toxin and MOG peptide are shown in FIG. 4.

INDUSTRIAL APPLICABILITY

The hydroxylated KRN7000 analogs developed by the present invention can induce the production of cytokine biased to the Th2 type, such as IL-4 and the like, more than KRN7000, and suppress production of Th1 type cytokine. Therefore, the present invention can provide use as therapeutic drugs for autoimmune diseases, antiallergic agents, as well as immunosuppressants.

Furthermore, IL-4 production can be potentiated more by pulsing dendritic cells with the hydroxylated glycolipid of the present invention and administering the dendritic cells.

This application is based on patent application No. 2012-173278 filed in Japan (filing date: Aug. 3, 2012), the contents of which are incorporated in full herein.

The invention claimed is:

1. A compound represented by the formula (I)

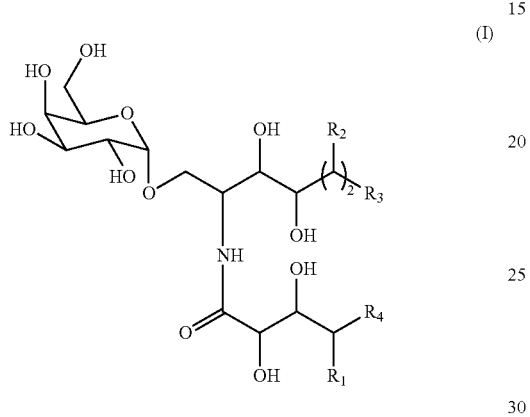

(I)

wherein
R$_1$ is a hydrogen atom or a hydroxyl group;
two R$_2$ are the same or different and each is a hydrogen atom or a hydroxyl group;
R$_3$ is a hydrocarbon group having 8-14 carbon atoms, which optionally has substituent(s); and
R$_4$ is a hydrocarbon group having 18-24 carbon atoms, which optionally has substituent(s), or a salt thereof.

2. The compound according to claim 1, wherein R$_3$ is a C$_{8-14}$ alkyl group, a C$_{8-14}$ alkenyl group or a C$_{8-14}$ alkynyl group, each of which optionally has substituent(s), or a salt thereof.

3. The compound according to claim 1, wherein R$_4$ is a C$_{18-24}$ alkyl group, a C$_{18-24}$ alkenyl group or a C$_{18-24}$ alkynyl group, each of which optionally has substituent(s), or a salt thereof.

4. The compound according to claim 1, wherein R$_1$ is a hydrogen atom, two R$_2$ are hydroxyl groups, R$_3$ is a C$_{8-14}$ alkyl group, and R$_4$ is a C$_{18-24}$ alkyl group, or a salt thereof.

5. The compound according to claim 1, wherein R$_1$ is a hydrogen atom, two R$_2$ are hydrogen atoms, R$_3$ is a C$_{8-14}$ alkyl group, and R$_4$ is a C$_{18-24}$ alkyl group, or a salt thereof.

6. The compound according to claim 1, wherein R$_1$ is a hydroxyl group, two R$_2$ are hydrogen atoms, R$_3$ is a C$_{8-14}$ alkyl group, and R$_4$ is a C$_{18-24}$ alkyl group, or a salt thereof.

7. The compound according to claim 1, which is

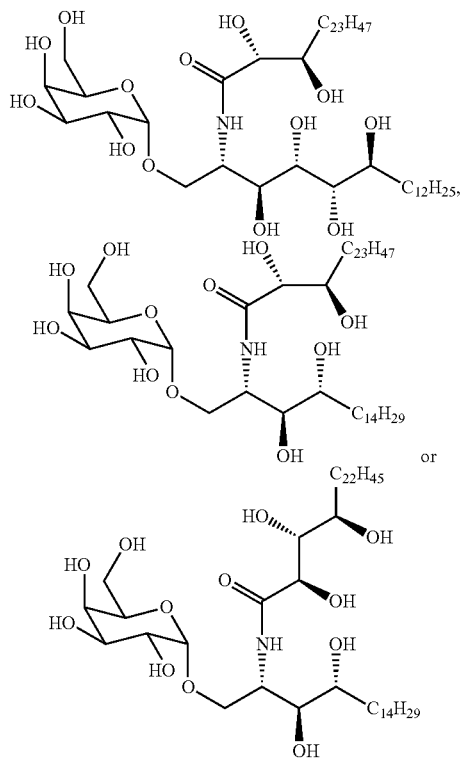

or a salt thereof.

8. A medicament comprising the compound according to claim 1, or a salt thereof.

9. A Th2 type cytokine secretion promoter comprising the compound according to claim 1, or a salt thereof.

10. The medicament according to claim 8, which is a therapeutic drug for an autoimmune disease.

11. The medicament according to claim 8, which is an immunosuppressant.

12. A human dendritic cell pulsed with the compound according to claim 1, or a salt thereof.

13. An immunosuppressant comprising the human dendritic cell according to claim 12.

14. A therapeutic drug for an autoimmune disease, comprising the human dendritic cell according to claim 12.

* * * * *